US011563165B2

(12) United States Patent
Tofail et al.

(10) Patent No.: US 11,563,165 B2
(45) Date of Patent: Jan. 24, 2023

(54) PIEZOELECTRIC DEVICE COMPRISING AN AMINO ACID CRYSTAL

(71) Applicant: UNIVERSITY OF LIMERICK, Limerick (IE)

(72) Inventors: Syed Ansar Tofail, Limerick (IE); Damien Thompson, Limerick (IE); Sarah Guerin, County Kerry (IE)

(73) Assignee: UNIVERSITY OF LIMERICK (*) Notice: Subject to any disclaimer, the term of this patent is extended or adjusted under 35 U.S.C. 154(b) by 525 days.

(21) Appl. No.: 16/606,127

(22) PCT Filed: Apr. 19, 2018

(86) PCT No.: PCT/EP2018/060084
§ 371 (c)(1),
(2) Date: Oct. 17, 2019

(87) PCT Pub. No.: WO2018/193050
PCT Pub. Date: Oct. 25, 2018

(65) Prior Publication Data
US 2020/0098971 A1    Mar. 26, 2020

(30) Foreign Application Priority Data
Apr. 20, 2017 (EP) .................... 17167368

(51) Int. Cl.
H01L 41/18 (2006.01)
G06N 10/00 (2022.01)
C07C 229/08 (2006.01)
G06N 5/04 (2006.01)
H01L 41/047 (2006.01)
H01L 41/08 (2006.01)
H01L 41/113 (2006.01)

(52) U.S. Cl.
CPC .......... H01L 41/183 (2013.01); C07C 229/08 (2013.01); G06N 5/04 (2013.01); G06N 10/00 (2019.01); H01L 41/047 (2013.01); H01L 41/0825 (2013.01); H01L 41/113 (2013.01); H01L 41/1132 (2013.01); C07B 2200/13 (2013.01)

(58) Field of Classification Search
CPC . H01L 41/183; H01L 41/047; H01L 41/0825; H01L 41/113; H01L 41/1132
See application file for complete search history.

(56) References Cited

PUBLICATIONS

Tylczynski Zbigniew et al; "Low-temperature phase transition in [gamma]-glycine single crystal Pyroelectric, piezoelectric, dielectric and elastic properties", Materials Chemistry and Physics, Elsevier SA, Switzerland, Taiwan, Republic of China, vol. 183, Aug. 16, 2016 (Aug. 16, 2016), pp. 254-262.

Ashok Kumar R et al; "Structural, dielectric and piezoelectric properties of nonlinear optical-glycine single crystals", Physica B: Condensed Matter, Elsevier, Amsterdam, NL, vol. 406, No. 13, Apr. 1, 2011 (Apr. 1, 2011), pp. 2594-2600.

Lemanov V V et al; "Piezoelectric properties of crystals of some protein aminoacids and their related compounds", Physics of the Solid State, Nauka/Interperiodica, MO, vol. 44, No. 10, Oct. 1, 2002 (Oct. 1, 2002), pp. 1929-1935.

(Continued)

Primary Examiner — Derek J Rosenau
(74) Attorney, Agent, or Firm — Clark Hill PLC; James R. Foley

(57) ABSTRACT

The present invention discloses a piezoelectric device comprising an amino acid crystal.

12 Claims, 15 Drawing Sheets

(56) References Cited

PUBLICATIONS

Bystrov V S et al; "Modeling of glycine polymorphic and switching properties", 2013 Joint IEEE International Symposium on Applications of Ferroelectric and Workshop on Piezoresponse Force Microscopy (ISAF/PFM), IEEE, Jul. 21, 2013 (Jul. 21, 2013), pp. 38-40.

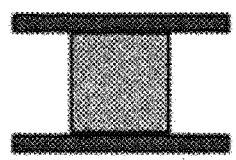
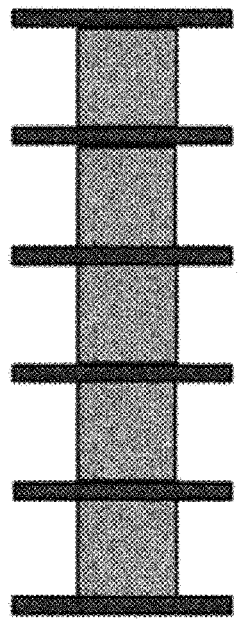
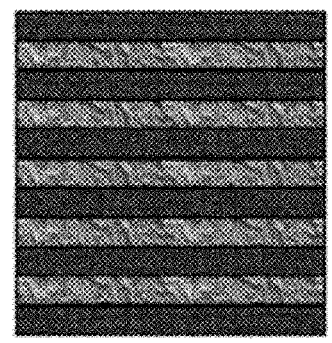
Figure 7A     Figure 7B     Figure 7C
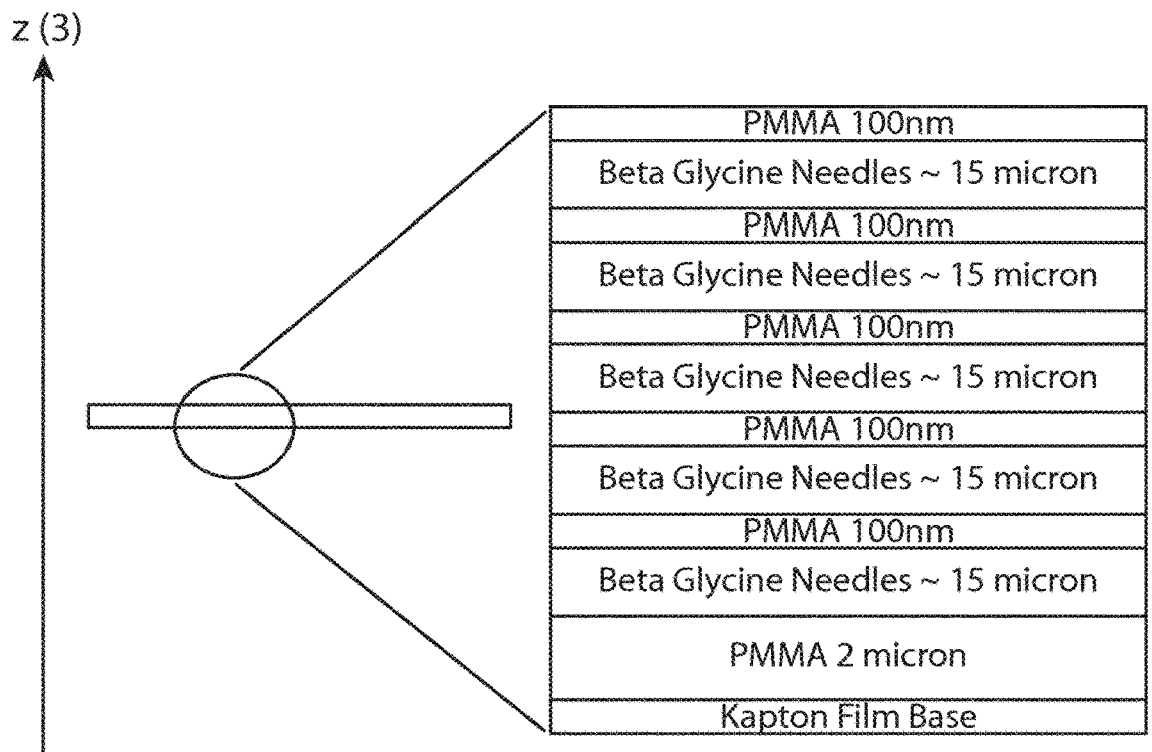
Figure 8A
*Device layers shown not to scale (a) L-Asparagine
$d_{16} = -13$ pm/V (b) L-Leucine
$d_{34} = 20$ pm/V

92°

94°

(c) L-Histidine
$d_{16} = 18$ pm/V (e) L-Methionine
$d_{34} = 15$ pm/V

97°

99°

(d) L-Aspartate
$d_{34} = 13$ pm/V (f) L-Isoleucine
$d_{34} = 25$ pm/V

101°

(g) L-Cysteine
$d_{22} = 11$ pm/V

109°

98°

PIEZOELECTRIC DEVICE COMPRISING AN AMINO ACID CRYSTAL

FIELD

The present invention relates to piezoelectric devices. More particularly, the present invention relates to a piezoelectric device comprising an organic material.

BACKGROUND

Piezoelectric materials are able to produce electricity in proportional to an applied mechanical strain, and conversely, deform linearly in the presence of an applied electric field. A variety of inorganic materials are known to exhibit relatively high piezoelectricity (for example between 20 and 800 pC/N). These include barium titanate ($BaTiO_3$), polyvinylidene fluoride (PVDF) and lead zirconate titanate (PZT). The high piezoelectricity of these inorganic materials is well understood, successfully engineered, and exploited technically in nanogenerators, biosensors, resonators, acoustics, and in scanning probe microscopy (SPM).

On the other hand, fibrous proteins such as collagen and elastin, bone, and some viruses have, to date, exhibited relatively modest piezoelectricity (for example between 0.1 pC/N and 10 pC/N). It is also known that deoxyribonucleic acid (DNA) is piezoelectric, but the origin of piezoelectricity in DNA remains unclear and its quantitative value uncertain.

The publication in the name of Tylczynski Zbigniew et al entitled "Low-temperature phase transition in [gamma] glycine single crystal. Pyroelectric, piezoelectric, dielectric and elastic properties", Materials chemistry and physics, Elsevier SA, Switzerland, Taiwan, Republic of China, vol. 183, 16 Aug. 2016 pages 254 to 262 simply describes the use of impedance spectroscopy to measure the piezoelectricity in gamma glycine crystals, with gamma glycine being described as a weak piezoelectric.

The publication in the name of Ashok Kumar et al entitled "Structural, dielectric and piezoelectric properties of non-linear optical-glycine single crystals", Physica B: Condensed Matter, Elsevier, Amsterdam, NL, vol. 406, no. 13, 1 Apr. 2011, pages 2594-2600, also describes measuring the piezoelectricity in gamma glycine crystals.

The publication in the name of Lemanov V V et al entitled "Piezoelectric properties of crystals of some protein amino acids and their related compounds", Physics of the solid state, Nauka/Interperiodica, Mo, vol. 44, no. 10, 1 Oct. 2002, pages 1929-1935 describes the use of radio-frequency pulses to qualitatively measure piezoelectricity in a number of amino acids.

Accordingly, it is an object of the present invention to provide a piezoelectric device comprising an organic material.

SUMMARY

According to one aspect of the invention there is provided, as set out in the appended claims, a piezoelectric device comprising:
a plurality of electrodes; and
an amino acid crystal coupled to the plurality of electrodes, wherein the geometry and the orientation of the amino acid crystal are configured to maximise the piezoelectric output of the device.

In one embodiment, the amino acid crystal comprises glycine.

In one embodiment, the amino acid crystal comprises β-glycine.

In one embodiment, the amino acid crystal comprises γ-glycine.

In one embodiment, the amino acid crystal comprises a crystal selected from the group of nineteen L-amino acid crystals.

In one embodiment, the amino acid crystal comprises a crystal selected from the group of nineteen L-amino acid crystals or the racemic crystal DL-Alanine.

In one embodiment, the amino acid crystal comprises a monoclinic amino acid crystal sliced to a geometry such that the ratio of length to width to thickness of the crystal substantially corresponds to 30:12:1 so as to induce resonance of the crystal in thickness shear mode.

In one embodiment, the orientation of the amino acid crystal is configured to make electrical contact with the plurality of electrodes along those crystallographic axes which have been determined to maximise the output of the device.

In one embodiment, the geometry of the amino acid crystal and the orientation of the amino acid crystal are determined from piezoelectric coefficients predicted by a quantum mechanical calculation performed on the amino acid crystal.

In one embodiment, the quantum mechanical calculation is based on Density Functional Theory (DFT).

The present invention also provides an electromechanical transducer comprising the piezoelectric device.

The present invention also provides a sensor comprising the piezoelectric device.

The present invention also provides an energy harvester comprising the piezoelectric device.

In one embodiment, the piezoelectric device is for use as an electromechanical transducer.

In one embodiment, the piezoelectric device is for use as a sensor.

In one embodiment, the piezoelectric device is for use as an energy harvester.

In one embodiment, the geometry and the orientation of the amino acid crystal are configured to maximise the output of the device.

In one embodiment, the amino acid crystal comprises a monoclinic amino acid needle slice wherein the ratio of length to width to thickness is substantially 30:12:1.

In one embodiment, the amino acid crystal is configured to make electrical contact along those axes which have been determined to maximise the output of the device.

According to another aspect of the invention there is provided, a piezoelectric device comprising an amino acid crystal.

According to another aspect of the invention there is provided a method for predicting at least one piezoelectric coefficient of a material comprising performing a quantum mechanical calculation on the material to determine the piezoelectric coefficient.

In one embodiment, the quantum mechanical calculation is based on Density Functional Theory (DFT).

In one embodiment, the at least one piezoelectric coefficient comprise one or more of: the elastic constant, the dielectric constant, the piezoelectric strain constant, the charge coefficient and the voltage constant.

In one embodiment, the elastic constant is calculated by extracting the diagonal matrix components of the 6×6 matrix stiffness tensor c:

$$C = \begin{pmatrix} c_{11} & c_{12} & c_{13} & c_{14} & c_{15} & c_{16} \\ c_{21} & c_{22} & c_{23} & c_{24} & c_{25} & c_{26} \\ c_{31} & c_{32} & c_{33} & c_{34} & c_{35} & c_{36} \\ c_{41} & c_{42} & c_{43} & c_{44} & c_{45} & c_{46} \\ c_{51} & c_{52} & c_{53} & c_{54} & c_{55} & c_{56} \\ c_{61} & c_{62} & c_{63} & c_{64} & c_{65} & c_{66} \end{pmatrix};$$

and wherein the stiffness tensor is calculated by a finite difference method.

In one embodiment, the piezoelectric strain coefficient $d_{ik}$ is calculated using the relationship:

$$d_{ik} = e_{ij}/c_{kj}$$

and wherein the piezoelectric response comprises:

$$d = \begin{pmatrix} d_{11} & d_{12} & d_{13} & d_{14} & d_{15} & d_{16} \\ d_{21} & d_{22} & d_{23} & d_{24} & d_{25} & d_{26} \\ d_{31} & d_{32} & d_{33} & d_{34} & d_{35} & d_{36} \end{pmatrix}$$

wherein $d_{11}$, $d_{22}$ and $d_{33}$ correspond to the longitudinal piezoelectric strain coefficients, and the rightmost three columns correspond to the shear piezoelectric strain coefficients.

In one embodiment, the voltage constant $g_{ij}$ is obtained by dividing the corresponding piezoelectric strain constant $d_{ij}$ by the relevant dielectric constant $\varepsilon_{ii}$, as shown in the equation:

$$g_{ik} = d_{ij}/\varepsilon_{ii}\varepsilon_o$$

In one embodiment, the material is an organic material. In another embodiment, the material is an inorganic material.

BRIEF DESCRIPTION OF THE DRAWINGS

The invention will be more clearly understood from the following description of an embodiment thereof, given by way of example only, with reference to the accompanying drawings, in which:—

FIG. 7A shows a schematic of an exemplary embodiment of a simple resonator and/or energy harvester using a single crystal amino acid in accordance with the present invention;

FIG. 7B shows a schematic of an exemplary embodiment of a stack actuator design using single amino acid crystals in accordance with the present invention;

FIG. 7C shows a schematic of another exemplary embodiment of a stack actuator design using poly-crystalline amino acid films;

FIG. 8A shows a schematic of an exemplary embodiment of an energy harvester in accordance with the present invention;

DETAILED DESCRIPTION OF THE DRAWINGS

Figure 1A:
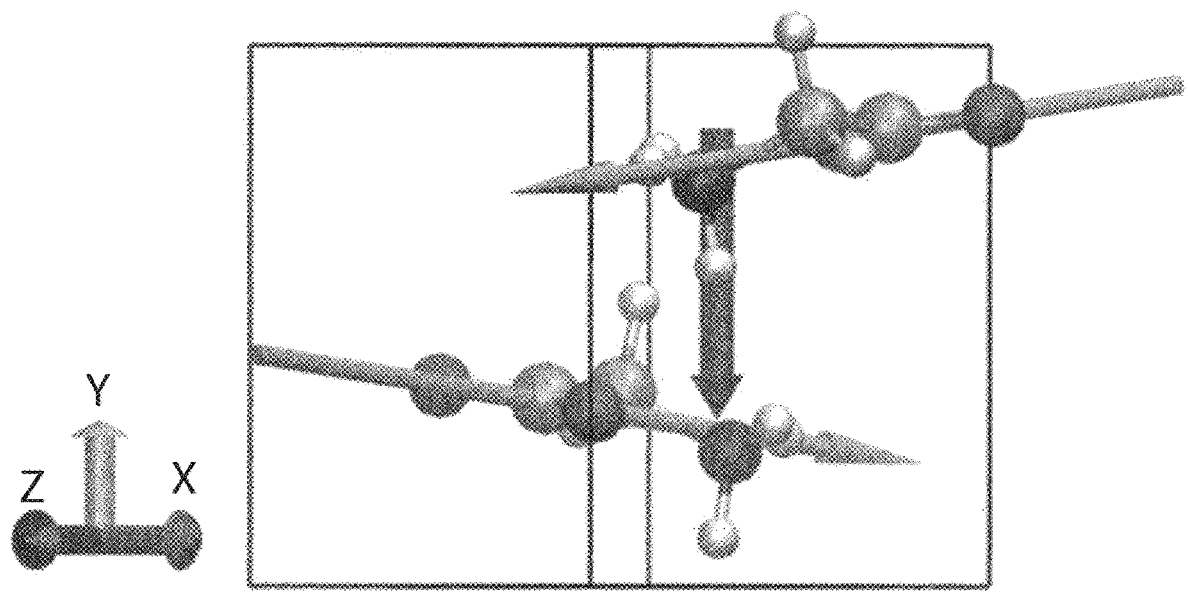
FIG. 1A shows the molecular packing which leads to piezoelectricity in β-glycine amino acid crystals.

Piezoelectricity is a third rank tensor property, which is known to be dependent on crystallographic directions. Accordingly, it will be appreciated that information regarding this directionality is required to accurately predict and measure technically useful piezoelectric coefficients for a range of organic piezoelectric materials.

Amino acids typically crystallize in orthorhombic and monoclinic space groups. The orthorhombic space group $P2_12_12_1$ generally does not allow any non-zero component of longitudinal piezoelectricity. Monoclinic crystals (space group 4 in Table 1 below) possess longitudinal piezoelectricity as well as both longitudinal and transverse shear components. All amino acids except glycine form stereoisomers (enantiomers) around the central alpha-carbon atom, meaning they can occur in L- and D-forms. Only L-forms are used by biological cells, but racemic crystals have (approximately) equal amounts of the two isomeric forms.

With regard to protein, nineteen of the twenty amino acids for building protein belong to chiral symmetry groups, meaning that they can exist in either left-handed (L) or right-handed (D) forms. Table 1 shows a table of these 19 L amino acids.

TABLE 1

| | 19 L amino acids | |
| --- | --- | --- |
| Crystal | Number of Atoms in Unit Cell | Space Group |
| L-Tyrosine | 96 | 19 |
| L-Glutamine | 80 | 19 |
| L-Glutamate | 76 | 19 |
| L-Threonine | 68 | 19 |

TABLE 1-continued

19 L amino acids

| Crystal | Number of Atoms in Unit Cell | Space Group |
|---|---|---|
| L-Proline | 68 | 19 |
| L-Serine | 56 | 19 |
| L-Alanine | 52 | 19 |
| L-Valine | 152 | 5 |
| L-Phenylalanine | 184 | 4 |
| L-Arginine | 104 | 4 |
| L-Lysine | 98 | 4 |
| L-Leucine | 88 | 4 |
| L-Isoleucine | 88 | 4 |
| L-Methionine | 80 | 4 |
| L-Cysteine | 56 | 4 |
| L-Histidine | 40 | 4 |
| L-Asparagine | 34 | 4 |
| L-Asparate | 32 | 4 |
| L-Tryptophan | 432 | 1 |

This chirality suggests that these nineteen amino acid crystal structures should exhibit a piezoelectric response. However, a known resonance spectrometry technique found that only eight of these nineteen amino acids actually exhibited a piezoelectric response in their pristine crystallised form at room temperature (295 K). A further seven amino acids exhibited piezoelectricity when crystallised in acidic or aqueous compounds. The remaining four amino acids however did not show any indication of piezoelectricity, due to the damping of elastic vibrations at the operating frequency of their setup. However, it should be noted that this known resonance spectrometry technique did not provide any quantitative measure of their piezoelectricity.

The racemic amino acid DL-Alanine, crystallized with a mixture of left-handed L-Alanine and right-handed D-Alanine amino acid molecules. DL-Alanine crystallizes in an orthorhombic structure that provides a non-zero longitudinal coefficient $d_{33}$. Piezoelectricity has been confirmed qualitatively in DL-Alanine single crystals, but never quantified.

The only non-chiral amino acid, glycine, crystallises in three distinct polymorphs namely, alpha (α), beta (β) and gamma (γ) glycine under ambient conditions. The crystallisation of α-glycine occurs in the centrosymmetric space group $P2_1/c$, which precludes piezoelectricity. On the other hand, β-glycine and γ-glycine belong to the non-centrosymmetric space groups $P2_1$ and $P3_2$ respectively, meaning that they should exhibit non-zero piezoelectric response at least in certain crystallographic directions. In this regard, the crystal symmetry of β and γ-glycine allows thirteen and eight non-zero piezoelectric coefficients respectively.

According to one aspect of the present invention, quantum mechanical calculations are employed to predict and quantify the piezoelectric coefficients in one or more of the ambient polymorphs of glycine, namely α, β and γ-glycine, as well as in the 19 L-amino acid crystals and the racemic crystal DL Alanine. In one embodiment of the invention, the quantum mechanical calculations of the piezoelectric coefficients are based on Density Functional Theory (DFT). The paragraphs below set out a summary of the values of a plurality of piezoelectric coefficients of these amino acids calculated using the DFT methodology of the present invention. The exact DFT methodology is then set out in later paragraphs.

Elastic Constants of the Glycine Polymorphs

The third-order material tensor, piezoelectricity, links the first-order induced electric displacement vector to the second-order stress tensor. Table 2 shows the elastic stiffness constants for the α, β and γ glycine polymorphs calculated through the use of the DFT methodology of the present invention. The calculated Young's Moduli in GPa are also shown.

TABLE 2

Computed elastic constants of the three ambient polymorphs of glycine

| Coefficient | α-glycine (GPa) | β-glycine (GPa) | γ-glycine (GPa) |
|---|---|---|---|
| $c_{11}$ | 53.7 | 55.5 | 25.0 |
| $c_{22}$ | 21.7 | 23.0 | 27.4 |
| $c_{33}$ | 71.5 | 69.3 | 77.8 |
| $c_{44}$ | 7.5 | 7.6 | 12.0 |
| $c_{55}$ | 16.3 | 15.6 | 12.5 |
| $c_{66}$ | 6.0 | 1.3 | 5.4 |
| Young's Modulus (GPa) | 30 | 15 | 28 |

It can be seen from the table that all but the longitudinal shear stress coefficient $c_{66}$ computed for achiral α-glycine are very similar to those of β-glycine, despite the fact that α-glycine is centrosymmetric and, thus, non-piezoelectric. The $c_{66}$ is four times larger in α-glycine than that in β-glycine.

The $c_{44}$ and $c_{66}$ values for β-glycine are relatively low (8 GPa and 1 GPa respectively), which suggests a high shear compliance and the possibility of a high shear piezoelectricity in this polymorph. On the other hand, γ-glycine shows higher values of $c_{44}$ and $c_{66}$, 12 GPa and 5 GPa respectively, indicating a lower shear compliance. It should be also noted that the elastic constants for all three glycine polymorphs are lower than those of typical inorganic piezoelectric materials. Thus, it will be appreciated that there is an inherent mechanical 'softness' in biological materials. This 'softness' in biological materials has many advantages in solid state device applications, in particular for flexible devices for energy harvesting.

Young's Modulus of the Glycine Polymorphs

Table 3 shows the Young's Moduli of the α, β and γ glycine polymorphs calculated through the use of the DFT methodology of the present invention, and compares these Young's Moduli values with experimentally observed values for the Young's Moduli of these three glycine polymorphs as well as values for the Young's Moduli of these three glycine polymorphs calculated by a conventional method, which uses Density Functional Perturbation Theory (DFPT) calculations with a slightly lower energy cut off (950 eV) and a Voight-Reuss average for estimating the elastic moduli.

TABLE 3

Calculated Young's Moduli of the three ambient polymorphs of glycine

| Glycine polymorph | Calculated value (GPa) | Experiment (GPa) | Other Calculations (GPa) |
|---|---|---|---|
| Alpha | 30 | 33 | 40 |
| Beta | 15 | — | — |
| Gamma | 28 | 28 | 19 |

Through the use of the DFT methodology of the present invention, a high predictability of results for the bulk crystal Young's Moduli is achieved, when compared with the Young's Moduli averaged from experimentally measured data across all crystal faces. The finite difference calculations obtained through the use of DFT deviate from bulk experimental values by 11% and 2% for α and γ-glycine respectively. It should be noted that this is significantly lower than the 20% and 32% deviations in those values calculated by the conventional method outlined above.

The similarity of the magnitudes of calculated Young's moduli of α and γ-glycine as shown in Table 3 corroborates with the physical appearance and handling of these polymorphs noted during experimental work. Both of these polymorphs present as hard but stable crystals of macroscopic dimension that are easy to handle. In contrast, β-glycine grows as fragile, microscopic needles. Aggregates of the β-glycine needles are relatively soft and brittle, which is also in line with the predicted Young's Moduli (approximately half that of γ-glycine).

Relative Permittivity of the Glycine Polymorphs

Piezoelectricity is directly related to the electric displacement vector. Bound charges from atomic nuclei and their respective electrons in a dielectric material separate slightly in the presence of an electric field. This induces a local electric dipole moment which is a product of the electric displacement and the bound charges. The relative permittivity of a material is a measure of its total dipole moment. In a linear anisotropic material, relative permittivity is a tensor. Table 4 shows the relative permittivity tensors of the α, β and γ glycine polymorphs calculated from DFT, in accordance with the present invention.

TABLE 4

Computed relative permittivity and dielectric constants of the three ambient polymorphs of glycine.

| Glycine Polymorph | $\varepsilon_{11}$ | $\varepsilon_{22}$ | $\varepsilon_{33}$ | $\varepsilon_r$ |
|---|---|---|---|---|
| Alpha | 2.74 | 2.19 | 2.60 | 2.51 |
| Beta | 2.71 | 2.17 | 2.58 | 2.49 |
| Gamma | 2.46 | 2.46 | 2.58 | 2.50 |

It should be noted that the values calculated for these glycine polymorphs are consistent with those of other amino acids (relative permittivity of 2.13-2.39) calculated using DFPT. The average dielectric constant calculated through the use of the DFT methodology of the present invention is 2.5 for glycine.

Charge and Strain Coefficients for the Glycine Polymorphs

Under the influence of a mechanical stress, a crystal undergoes deformation causing ions in the crystal to shift from their equilibrium lattice positions. This creates electrical dipole moments. For a net polarisation to develop, it will be appreciated that the dipoles formed within the unit cell of the crystal must not cancel out. As α-glycine is a centrosymmetric crystal, it experiences symmetrical movement of ions. Thus, the dipoles in the unit cell cancel each other resulting in no net polarisation due to strain. However, in the absence of a centre of symmetry, a mechanical deformation of the crystal creates non-symmetrical movement of these ions, which ultimately creates a net polarisation, as is shown in FIG. 1.

In this regard, FIG. 1A shows the intramolecular dipoles (green) in the unit cell of beta glycine, which contribute to the spontaneous polarization (red) along the 2-axis. This net polarization along the crystallographic b axis corresponds to a finite $e_{22}$ piezoelectric coefficient. In this figure, molecules are shown in CPK representation and carbon atoms are coloured cyan, hydrogen atoms are white, oxygen atoms are red and nitrogen atoms are navy blue. It should further be noted that crystallographic a, b, and c axes of the crystals have been chosen to align with arbitrarily chosen 1, 2 and 3 axes respectively.

Figure 1B:
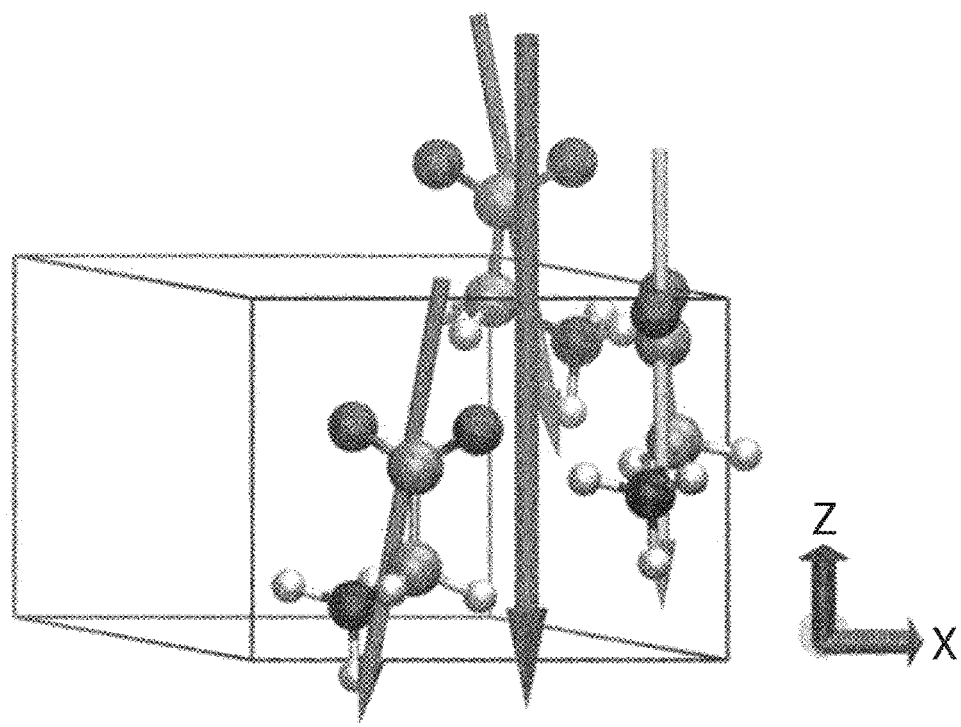
FIG. 1B shows the molecular packing which leads to piezoelectricity in γ-glycine amino acid crystals.

FIG. 1B shows the intramolecular dipoles (green) in the unit cell of gamma glycine, which contribute to the spontaneous polarization (red) along the 3-axis. This net polarization along the crystallographic c axis corresponds to a finite $e_{33}$ piezoelectric coefficient.

Figure 2A:
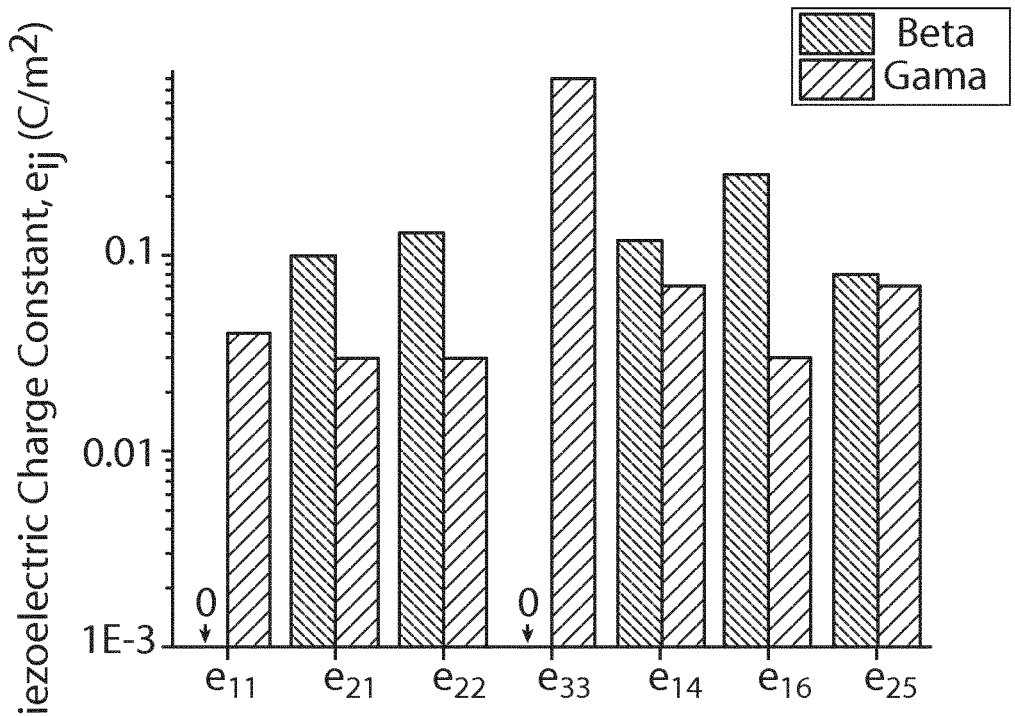
FIG. 2A shows a graph of the calculated charge coefficients in respect of β- and γ-glycine.
Figure 2B:
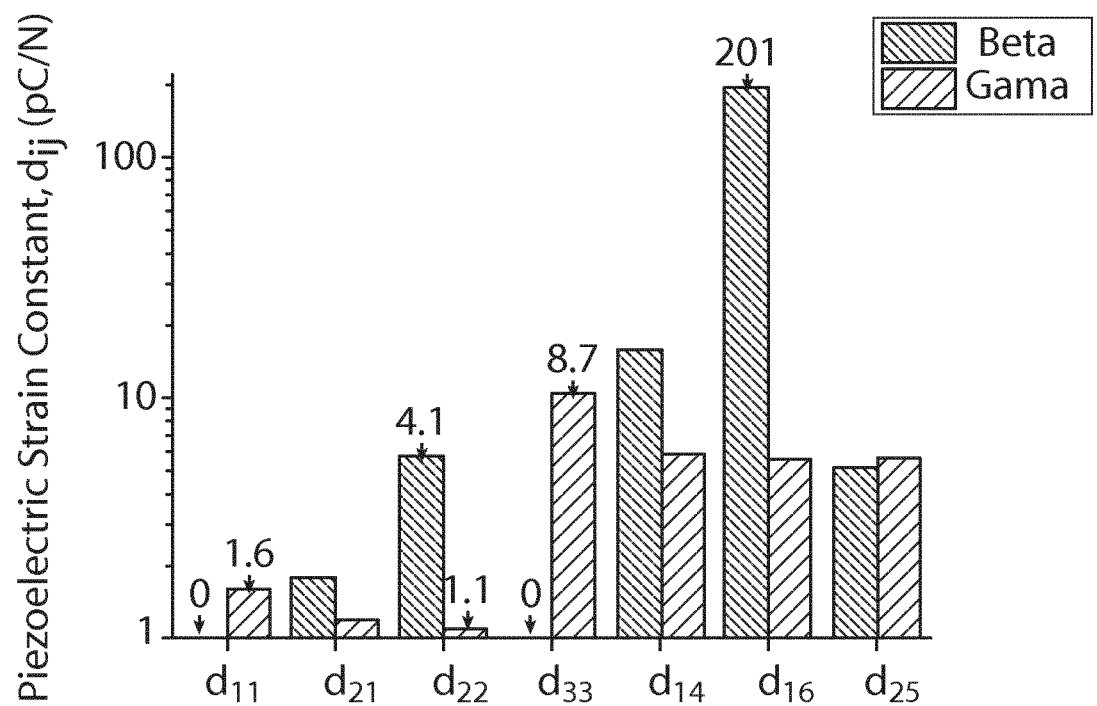
FIG. 2B shows a graph of the calculated strain coefficients in respect of β- and γ-glycine.
Figure 2C:
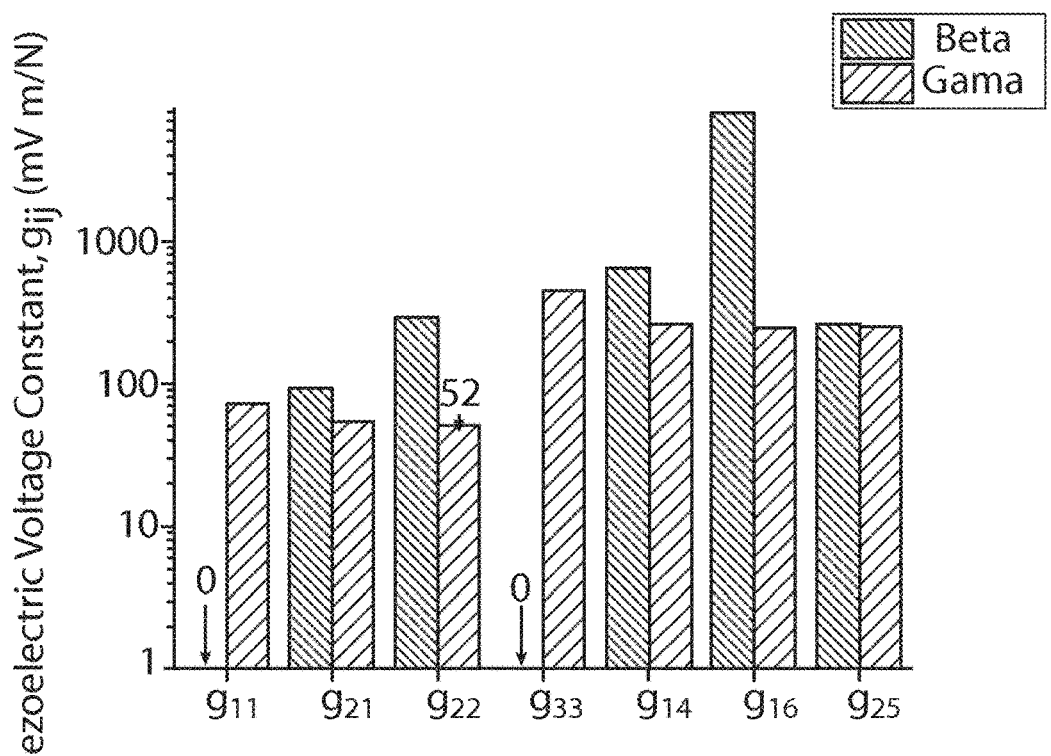
FIG. 2C shows a graph of the calculated piezoelectric voltage constants in respect of β- and γ-glycine.

In accordance with the present invention, the piezoelectric charge and strain coefficients have been calculated from atomistic simulations of β- and γ-glycine using DFT. FIG. 2A shows a graph of the calculated charge coefficients in respect of β- and γ-glycine, while FIG. 2B shows a graph of the calculated strain coefficients in respect of β- and γ-glycine (experimentally measured values are marked above relevant columns). FIG. 2C shows a graph of the calculated piezoelectric voltage constants in respect of β- and γ-glycine (experimentally measured values are marked above relevant columns).

The crystal symmetry of γ-glycine is trigonal $P3_2$ (space group 145, point group 3) which possesses three longitudinal, one transverse and two shear non-zero constants.

As can be seen from FIG. 2B, the piezoelectric longitudinal strain coefficient $d_{33}$ of γ-glycine (10.4 pC/N) along an arbitrarily chosen 3-axis (considered as parallel to the crystallographic c-axis, FIG. 1B) calculated using DFT is comparable to the highest reported piezo-response of zinc oxide. This value is also comparable to the highest piezoelectric coefficient experimentally measured in γ-glycine. Note also the remarkably high $d_{16}$ coefficient in β glycine, which was experimentally validated.

Contrastingly, β-glycine crystallises in monoclinic $P2_1$ symmetry (space group 4, point group 2), which possesses one longitudinal, two transverse, and five shear non-zero coefficients. As can be seen from FIG. 2B, the piezoelectric longitudinal strain coefficient $d_{22}$ of β-glycine (5.4 pC/N) along an arbitrarily chosen 3-axis (considered as parallel to the crystallographic b-axis, FIG. 1A) calculated using DFT is approximately one half of the highest longitudinal strain coefficient of γ-glycine. This $d_{22}$ coefficient of β-glycine is also experimentally verifiable.

It will be appreciated that the magnitude of shear piezoelectricity in glycine is of particular importance. This previously unknown property is predicted by the DFT calculations of the present invention. The longitudinal-shear and transverse shear coefficients of γ-glycine are of the same order as the longitudinal values and, while still lower than its $d_{33}$ coefficient, they are 5-7 times higher than the $d_{11}$ and the $d_{22}$ coefficients.

This trend of high longitudinal and transverse shear piezoelectricity is maintained in β-glycine. As can be seen from FIGS. 2A, 2B and 2C, both the longitudinal-shear and transverse shear piezoelectric coefficients of β-glycine can surpass the magnitudes of any corresponding piezoelectricity coefficient of γ-glycine. For example, according to the DFT calculations of the present invention, the transverse shear coefficient $d_{16}$ of β-glycine is 195 pC/N. This value is two orders of magnitude higher than the maximum piezoelectricity reported for collagen, almost 20 times higher than experimentally measured magnitude of piezoelectricity in γ-glycine, around 6-8 times higher than the known piezoelectric strain coefficients of any forms of PVDF polymers, about double of the coefficients of classical perovskite ceramic $BaTiO_3$ and comparable to those of soft-PZT ceramics.

The potential electrical energy that could be harvested from β-glycine is measured through the piezoelectric voltage constants. This is an important figure of merit (FoM) for sensor applications, in particular accelerometers and other pressure sensors. As can be seen from FIG. 2C, the relatively low permittivities of the glycine polymorphs lead to large voltage constants, which are a measure of the extent of strain for a given density of electrical polarisation. Conventional perovskite-based ceramics provide large strain but at the cost of large polarisation due to their very high dielectric constants. However, a combination of large strain and low polarisation is ideal for sensors and piezoelectric energy harvesting.

The results of the piezoelectric coefficients calculated in accordance with the present invention indicate that both γ- and β-glycine are capable of high voltage constants. The highest values are 0.46 V m/N for γ-glycine and 8.13 V m/N for β-glycine respectively. For comparison, PZT-based ceramics have reported voltage constants as high as 0.04 V m/N. Other studies have reported values of up to 0.54 V m/N for single crystals of $BiB_3O_6$. This suggests that both γ- and β-glycine are excellent candidates for use in high-performance sensing and transduction applications.

Experimental Validation of Quantum Mechanical Prediction

The DFT calculations of the piezoelectric coefficients performed in accordance with the present invention have been validated by experimental piezoelectricity measurements, as set out in detail below. The results indicate an excellent predictability of the quantum mechanical calculations of piezoelectric coefficients for γ-glycine.

For experimental validation, crystals of both γ- and β-glycine were grown. As β-glycine is a metastable polymorph, it can transform into more stable α and γ crystals under ambient conditions. X-Ray Diffraction and Raman Spectroscopy were used to confirm the presence of β-glycine prior to during, and after piezoelectric measurements. Polymorphs were also examined using scanning electron microscopy and optical microscopy.

The longitudinal component $d_{33}$ was measured using a piezometer with a quasi-static force applied to the (001) plane along the crystallographic c-axis of γ-glycine single crystals. This quasi-static measurement of the $d_{33}$ coefficient of 9.93 pm/V versus the predicted value of 10.4 pmN obtained by the DFT calculations compares well with microscopic measurements by PFM (10 pm/V). The measured value of the longitudinal strain coefficient $d_{11}$ of γ-glycine was 1.7 pmN, compared to a value of 1.6 pmN obtained by the DFT calculations. The measured value of the longitudinal strain coefficient $d_{22}$ of γ-glycine was −1.1 pmN, which is the same as the value for the coefficient obtained by the DFT calculations.

Figure 3A:
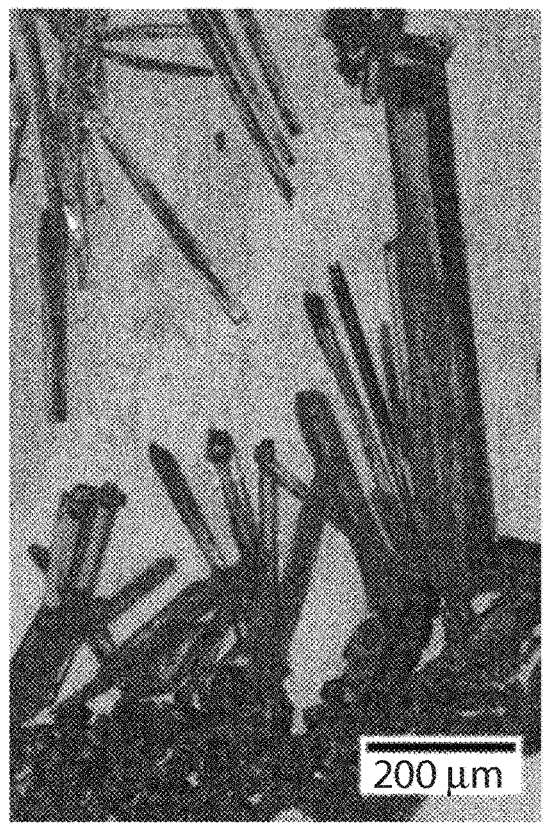
FIG. 3A shows an optical micrograph of β glycine needles.
Figure 3B:
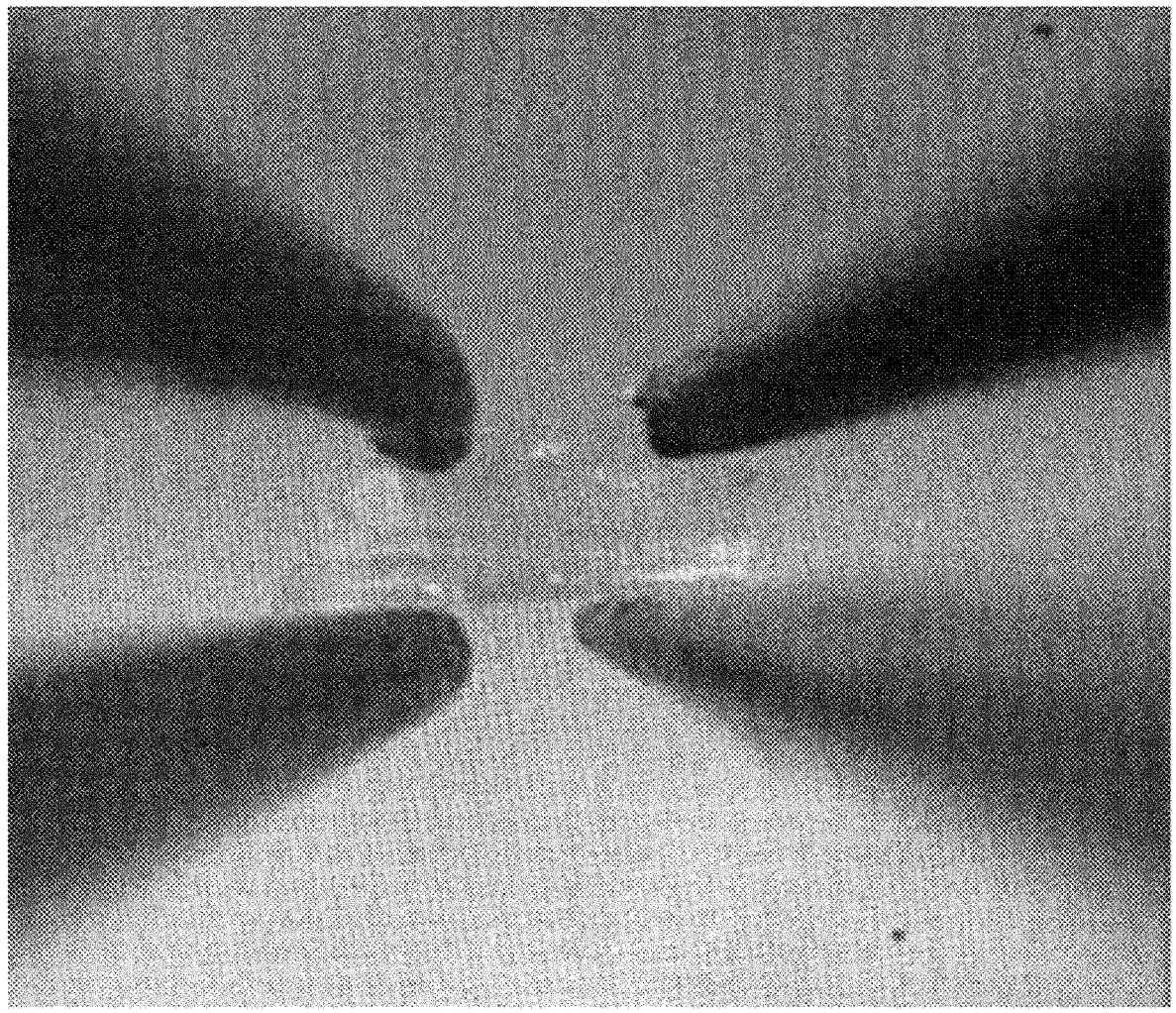
FIG. 3B shows a photo of a sliced glycine needle held together in a four-point probe configuration.

It should be appreciated that the measurement of the $d_{16}$ coefficient for β-glycine was non-trivial, due to the small size and low symmetry involved and the generation of a shear mode that would allow such measurement. This was achieved by means of a resonance method of piezoelectricity measurements using samples carefully sliced from β-glycine microcrystals (as per FIG. 3A), and held together in a four-point probe configuration as shown in FIG. 3B, where each probe has a 3.5 micron radius tip. These probes were connected to an impedance analyser which passed current at sweeping frequencies.

Electromechanical coupling at the sample's natural frequency caused maximum and minimum impedance peaks in thickness shear mode, from which a value of 1.02 GPa was obtained for the shear modulus $c_{66}$ (versus a predicted value of 1.31 GPa obtained by the DFT calculations), and a value of 0.97 was obtained for the electromechanical coupling constant. A capacitance measurement across the piezoelectric 1-axis (across which microprobes are positioned for resonance measurements) allowed a measurement of the relative permittivity along this plane ($\varepsilon_{11}$) as 3.21 (versus a predicted value of 2.7 obtained by the DFT calculations).

For $d_{22}$ measurements in β-glycine, a similar technique was used, but on the (010) plane along the crystallographic b-axis. In a similar way, the longitudinal $d_{22}$ value in β-glycine crystals was measured to be approximately 4.1 pC/N, versus a predicted value of 5.7 pC/N obtained by the DFT calculations.

Combining the values of shear modulus, permittivity and electromechanical coupling for β-glycine, a $d_{16}$ value of 178 pm/V±11 pm/V was experimentally obtained. While traditional resonance studies on inorganic piezoelectric ceramics and films can achieve far lower experimental error, it should be noted that the experimentally measured $d_{16}$ value in β-glycine is remarkably close to the value of $d_{16}$ of 195 pC/N predicted by DFT. The experimental $d_{16}$ value depends heavily on the measured thickness of the sample, which can cause significant fluctuations in the experimental relative permittivity. Given that the $d_{16}$ values of the α and γ polymorphs are 0 and 6 pm/V respectively, the smaller experimental value can also be attributed to the resonance measurements being carried out on di-phasic slices at room temperature and humidity.

Figure 4:
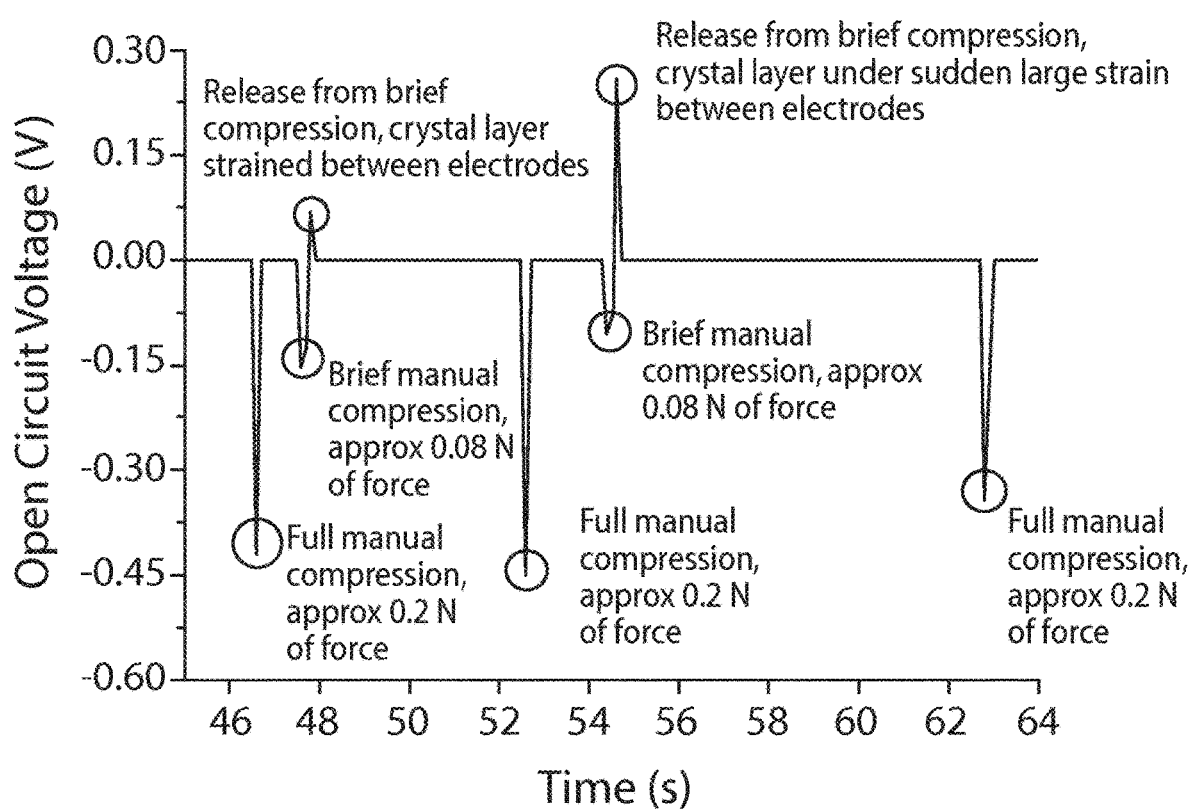
FIG. 4 shows the open circuit voltage response of a layer of γ-glycine seed crystals, orientated along the crystallographic 2-axis.

In order to validate the voltage coefficients predicated by the DFT calculations, a layer of γ-glycine seed crystals was compressed between electrodes of area 324 $mm^2$, under a force of 0.172 N. A maximum open circuit voltage measurement of 0.45 V was obtained, as shown in FIG. 2C. This corresponds to a voltage constant of 0.047 V m/N, just short of the predicted $g_{22}$ value of 0.051 V m/N. FIG. 4 shows the open circuit voltage response of the layer of γ-glycine seed crystals, orientated along the crystallographic 2-axis. Manual force is applied along the crystallographic 2-axis over time.

Supramolecular Packing and Piezoelectric Response of β and γ Glycine

It should be noted that the permittivities of β- and γ-glycine are very similar, all between 2 and 3. Thus, it is clear that the differences in permittivity are not the only factor contributing numerically to the large differences in the piezoelectric constants for these two polymorphs. FIG. 1 illustrates that the different molecular packing patterns changes the planes and directions along which the zwitterionic dipoles align between molecules within the lattice (intermolecular) and between lattices (intramolecular). This results in a net polarisation vector that may contribute, together with stiffness, towards the overall electromechanical coupling and piezoelectric coefficient.

It can be seen from Table 2 that the stiffness coefficients are numerically very close for both structures. The only stark contrast is in the coefficient $c_{11}$, which for β-glycine (56 GPa) is double that of γ-glycine (25 GPa). The present inventors believe this to be due to the 120° rhombohedral angle in γ-glycine, which allows a greater freedom of movement of molecules along the 1-axis, and hence lower stiffness. A similar observation can be made in β-glycine, which has a relatively small stiffness value of 1.3 GPa for its $c_{66}$ coefficient, the lowest among all stiffness values in α-, β- and γ-glycine. The monoclinic angle of 112° in β-glycine is also the largest among all the amino acids. As this is the angle that lies between the 1- and 3-axes, it allows for a large shear deformation around the 3-axis when an electric field is applied in the 1 direction, as shown in FIG. 1. This hypothesis also indicates that the highest piezoelectric constant of 195 pC/N ($d_{16}$ in β-glycine) is due mainly to the relatively small $c_{66}$ value of 1.3 GPa.

This point can be further illustrated through a comparison of the longitudinal piezoelectric coefficients $d_{22}$ of β-glycine (−5.7 pC/N) and $d_{33}$ in γ-glycine (−10.4 pC/N). Although the unit cell of γ-glycine has three glycine molecules and β-glycine has two, the volume density of the molecules in these two polymorphs is comparable (within 7% of each other). For polarisation along the b-axis of the (010) plane in β-glycine, the area is almost half (28 Å$^2$) that of the (001) plane in γ-glycine (52 Å$^2$). The net dipole along the b-axis in β-glycine is 3.2 D, which is far smaller than that along the c-axis of γ-glycine (40 D, see FIG. 1).

Hence the inventors have deduced that the unusually high $d_{16}$ piezoelectric coefficient in β-glycine originate from an efficient packing of the molecules along certain crystallographic planes and directions. High polarisation over a relatively small area in which molecules are (relatively) loosely packed around the monoclinic angle lowers the shear stiffness. The interplay between molecular packing and stiffness can be understood from the phenomenology that a solid would resist deformation that causes strain. Within the elastic limit the stress will be proportional to this strain in accordance with Hooke's law. Stress is the force that would resist this strain in a unit area of packing of molecules, and so for a given deformation, the stress is defined by the packing of the area by the solid. Thus, it can be concluded that the piezoelectricity in these small organic crystals is dependent on three main material properties, namely the density, the elasticity, and the permittivity of the material. These properties depend on the material's unit cell, as does the available charge that can be distributed per unit area. Thus, the overall piezoelectric response is pre-programmed in the individual supramolecular amino acid crystal structures.

Experimental Validation of L-Amino Acids

Figure 10:
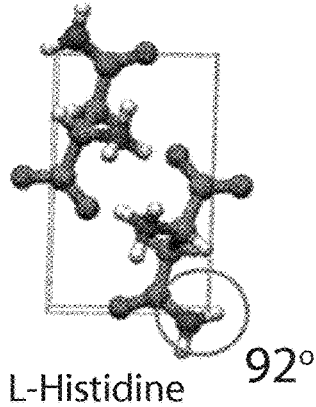
FIG. 10 shows the seven smallest monoclinic L-amino acid crystals, detailing their crystal packing, monoclinic angle, and highest predicted piezoelectric strain constant.
Figure 10:
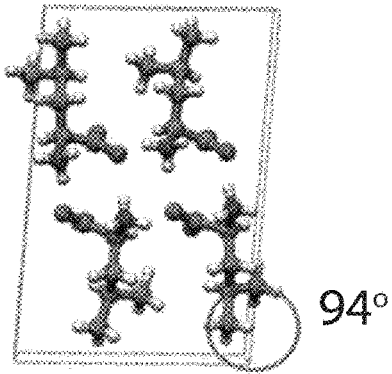
Figure 10:
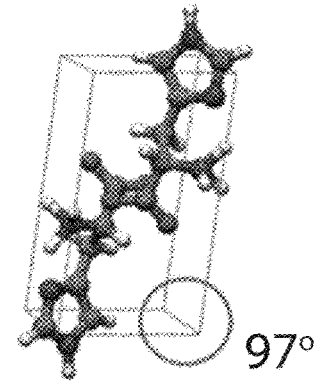
Figure 10:
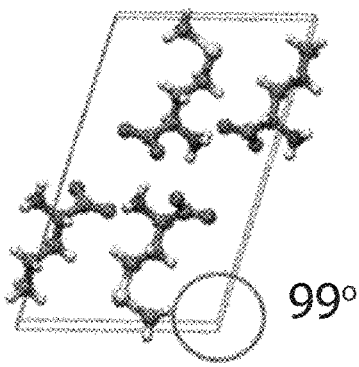
Figure 10:
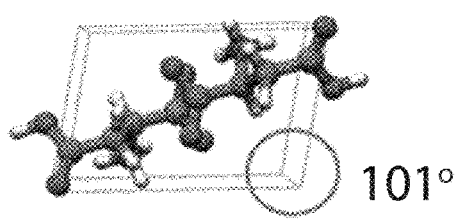
Figure 10:
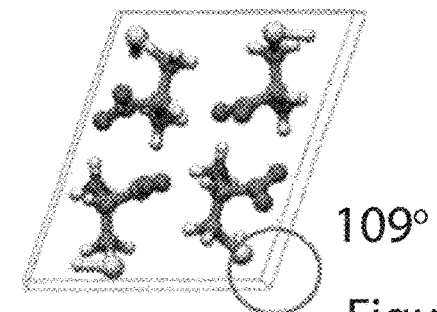
Figure 10:
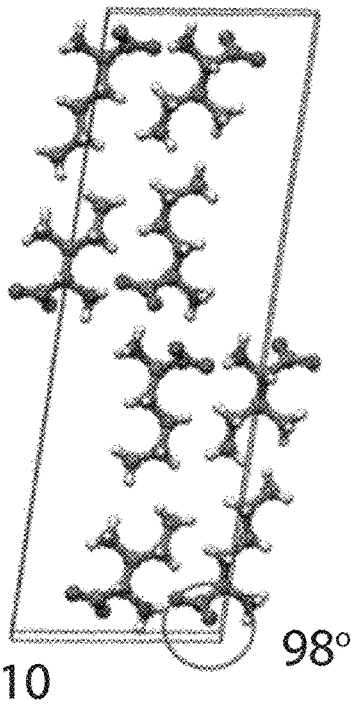

For small monoclinic L-amino acids, the lowest calculated stiffness value ($c_{44}$ or $c_{66}$ depending on the orientation of the unit cell) is consistently about the monoclinic axis. The lowest of these belong to L-Leucine ($c_{44}$=1.06 GPa) and L-Isoleucine ($c_{44}$=0.37 GPa), which are the only amino acids with simple alkyl-only side chains. In a similar manner to β-glycine, this relatively low stiffness results in a higher than expected shear piezoelectric strain constant ($d_{34}$=25 pm/V and 20 pm/V for Isoleucine and Leucine respectively), and voltage constants of approximately 1 V m/N. These are still an order of magnitude smaller than the 8134 mV m/N predicted for β-glycine but more than twice the $g_{33}$=455 mV m/N of γ-glycine. FIG. 10 shows the seven smallest monoclinic L-amino acid crystals, detailing their crystal packing, monoclinic angle, and highest predicted piezoelectric strain constant. Carbon atoms are coloured grey, hydrogen atoms are white, oxygen atoms are red, nitrogen atoms are blue and sulphur atoms are yellow.

Experimental Validation of Polycrystalline Amino Acid Films

Figure 11:
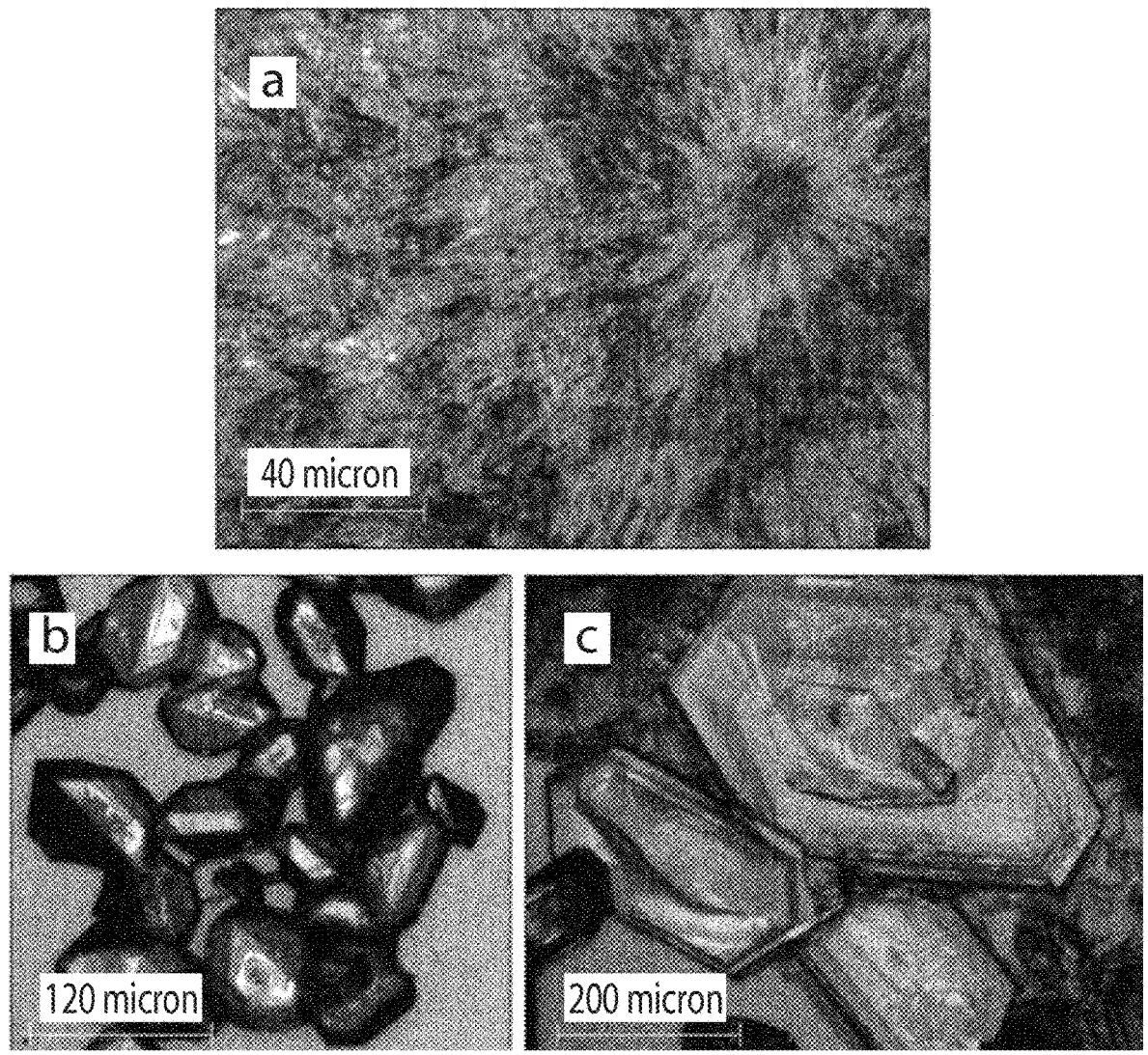
FIG. 11 shows L-Threonine, L-Alanine and hydroxy-L-proline crystal films grown from aqueous solution.

For experimental validation of amino acid films, amino acid films were all grown from saturated aqueous solutions. The crystal films showed remarkable growth dynamics, particularly when compared to the single crystal growth using similar methods. This was observed using brightfield (optical) microscopy. FIG. 11(a) shows L-Threonine grown from aqueous solution, FIG. 11(b) shows L-Alanine grown from aqueous solution, and FIG. 11 (c) shows hydroxy-L-proline crystal films grown from aqueous solution.

L-Threonine crystals grew as dense, high aspect ratio needle clusters that grew from a number of nucleation sites over a 2 cm×2 cm area. L-Alanine crystals differed substantially from their single crystals when grown in film form, forming sporadic clusters of low aspect ratio crystals, still visible to the naked eye. Hydroxy-L-proline crystals were very similar in size and aspect ratio in film form to single crystals, but also grew in dense, warped clusters, with few isolated fully formed monoclinic crystals. Single crystals of each amino acid formed within the respective drop cast solutions within an hour, and films formed after complete droplet evaporation over 24 hours. Transmission X-Ray Diffraction (XRD) was used to confirm the film compositions, and Scanning Electron Microscopy (SEM) was used to characterise the cross section of the films, showing the different orientations of single crystals within the aggregate structures. The broad diffraction peaks of L-Threonine crystal films was noted, which is consistent with the high degree of poly-crystallinity observed in the samples.

The effective longitudinal piezoelectric constants of the polycrystalline amino acid films were measured using a commercial piezometer with an accuracy of 0.01 pC/N. Hydroxy-L-Proline crystal films give consistent piezoelectric constants of ±1 pC/N, approximately one third of the predicted $d_{14}$ value for single crystals obtained by the DFT calculations. The maximum recorded value for hydroxy-L-proline crystal films was 2.48 pC/N. Both L-Threonine and L-Alanine showed order of magnitude lower measured effective piezoelectric constants of ±0.1 pC/N. The non-zero value of this modest response was confirmed with a polarity switch on inversion of the sample. Though small compared to other measurements of undoped amino acids, it is of the same order of the shear response of a number of biopolymers.

For L-Threonine and L-Alanine, the modest measured values are much less than their shear piezoelectric constants of 4-6 pC/N predicted by the DFT calculations. The relatively high longitudinal response of hydroxy-L-proline films is likely to have a number of sources. The most likely is simply that hydroxy-L-proline crystals have the highest predicted single crystal piezoelectric constants, and therefore are more likely to have a measurable longitudinal response in aggregate form, similar to tetragonal lysozyme films. However, from a review of the brightfield microscopy images, it is clear that Hydroxy-L-Proline crystals also appear to warp the most during film formation. Epitaxial or inter-crystalline strain could slightly alter the symmetry of the single crystals, allowing for an induced longitudinal polarisation, or an increased shear polarisation when stressed.

The effective longitudinal piezoelectricity in hydroxy-L-proline crystal films is of similar magnitude to X-cut quartz, and can therefore be exploited for sensing and energy harvesting applications. These films could in principle therefore generate an open circuit piezoelectric voltage as high as γ-glycine or phage viruses. The predicted single crystal piezoelectric voltage constants for the 7 orthorhombic L-amino acids are shown in Table 5 below. All values are in V m/N. The orientation of the hydroxy-L-proline crystals is with the longitudinal 3 axis perpendicular to the substrate, whereas the L-Threonine crystals are in randomly oriented clusters. The alignment of the hydroxy-L-proline crystals is more like to favour a measurable piezoelectric response, due to alignment of the induced single crystal dipole moments when stressed.

TABLE 5

Predicted piezoelectric voltage constants for the 7 orthorhombic L-amino acids.

| Crystal | $g_{14}$ | $g_{25}$ | $g_{36}$ |
|---|---|---|---|
| L-Threonine | 0.18 | 0.16 | 0.23 |
| L-Tyrosine | 0.24 | 0.46 | 0.27 |
| L-Glutamine | 0.09 | 0.18 | 0.54 |
| L-Glutamate | 0.03 | 0.08 | 0.15 |
| L-Serine | 0.22 | 0.20 | 0.14 |
| Hydroxy-L-Proline | 0.18 | 1.31 | 0.21 |
| L-Alanine | 0.30 | 0.18 | 0.30 |

By dividing the piezoelectric charge constants in C/m² by the elastic stiffness constants in GPa, the piezoelectric strain constants in pC/N (pm/V) is obtained. These constants can be verified experimentally using quasi-static methods, or with impedance spectroscopy. The three transverse shear piezoelectric strain constants predicted by the DFT calculations for the three most abundant L-amino acids in collagen, range in absolute value from <1 pC/N (L-proline) to 28 pC/N (hydroxy-L-proline). Using the same methods, a measured absolute $d_{25}$ value of 22-29 pC/N in Y-cut hydroxy-L-proline crystals is obtained, which agrees very well with the value of 28 pC/N obtained from the DFT calculations, and supports the prediction that the simple addition of an —OH can potentially increase the piezoelectric constant by two orders of magnitude.

Figure 12:
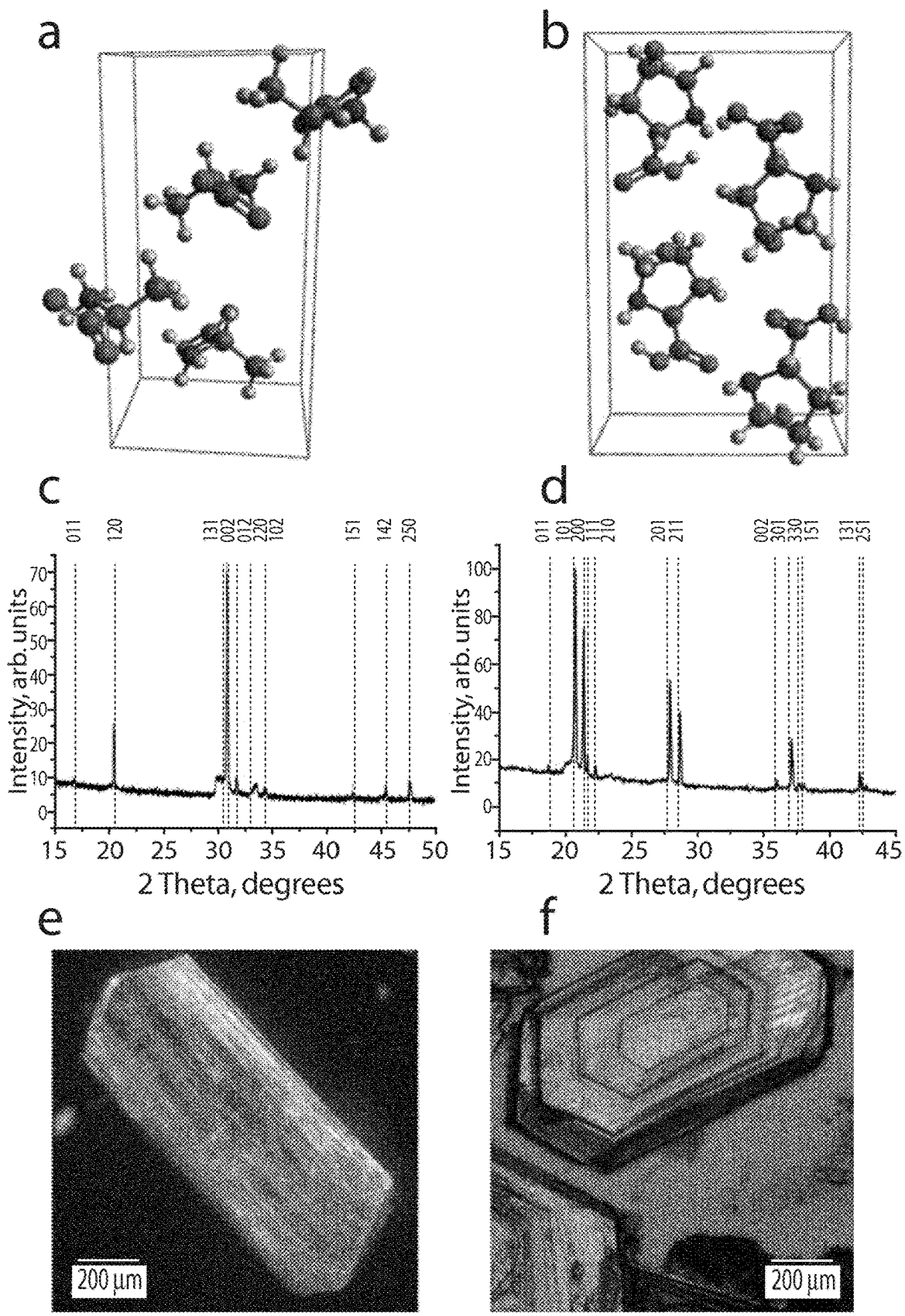
FIG. 12 shows the characterization of amino acid single crystals of L-alanine and hydroxy-L-proline used for piezoelectric measurements.

FIG. 12 shows the characterization of amino acid single crystals of L-alanine and hydroxy-L-proline used for piezoelectric measurements. In this regard, FIG. 12a shows unit cells of L-alanine used for quantum mechanical calculations, while FIG. 12b shows unit cells of hydroxy-L-proline used for quantum mechanical calculations. FIG. 12c shows the Measured X-Ray Diffraction (XRD) spectra of L-alanine crystals, while FIG. 12d shows the Measured X-Ray Diffraction spectra of hydroxy-L-proline crystals. The red dashed lines indicate peak assignments made using ICDD structures #00-028-1508 and #00-034-1720. FIG. 12e shows an optical image of L-alanine monoclinic crystals, while FIG. 12f shows an optical image of hydroxy-L-proline monoclinic crystals.

Experimental Validation of the Racemic Crystal of the Amino Acid DL-Alanine

The racemic amino acid DL-Alanine is crystallized with a mixture of left-handed L-Alanine and right-handed D-Alanine amino acid molecules. DL-Alanine crystallizes in an orthorhombic structure that provides a non-zero longitudinal coefficient $d_{33}$. In experiments which were performed on DL-Alanine, a longitudinal piezoelectric response of up to 5 pC/N was measured and open circuit voltages as large as 0.8 V were generated by manually compressing DL-Alanine films. Piezoelectric domains with 180° phase shifts were also observed in DL-Alanine single crystals, indicating the possibility of polarization switching similar to a classical ferroelectric material.

When the crystals were grown on copper substrates, preliminary $d_{33}$ measurements averaging +4.1 pC/N and −3.9 pC/N were recorded, with the polarity change on inverting the sample indicative of a genuine longitudinal piezoelectric response. The maximum recorded piezoelectric response was 4.8 pC/N, which is double that measured for samples on ITO glass, and the magnitudes of the positive and negative measurements are in good agreement.

A systematic investigation was also carried out into the longitudinal response of DL-Alanine crystalline films drop cast onto copper films. The highest individual recorded piezoresponse was 3.5 pC/N, with average values ranging from 1.1 pC/N to 2.6 pC/N. Percentage standard deviations across each film were in the range of 6-33%. The standard deviation between films was found to be similar in the upright (37%) and inverted (34%) configurations. It was noted that the piezoelectric response across each film was sensitive to small changes in measurement zones. The highest recorded measurements are close to the average value (4 pC/N) of the three predicted orthogonal responses for DL-Alanine single crystals when stressed along the 3 axis. This value is similar to the piezoelectric constants of zinc oxide and aluminium nitrate, and double that of X-cut quartz. The different orientations of the crystals in the film, as evidenced by XRD and electron microscopy, mean that different faces of the crystals are in contact with the piezometer electrodes, resulting in a combined $d_{31}$, $d_{32}$ and $d_{33}$ response that varies from point to point. Due to the degree of randomness in the crystal growth, all three $d_{31}$, $d_{32}$ and $d_{33}$ constants are contributing to the measured piezoelectric response. Initial measurements of up to 4.8 pC/N suggest that the highest single crystal $d_{33}$ constant of 10.3 pC/N predicted by the DFT calculation is indeed contributing to the measurements, but it is being diluted by the orthogonal responses.

Figure 13:
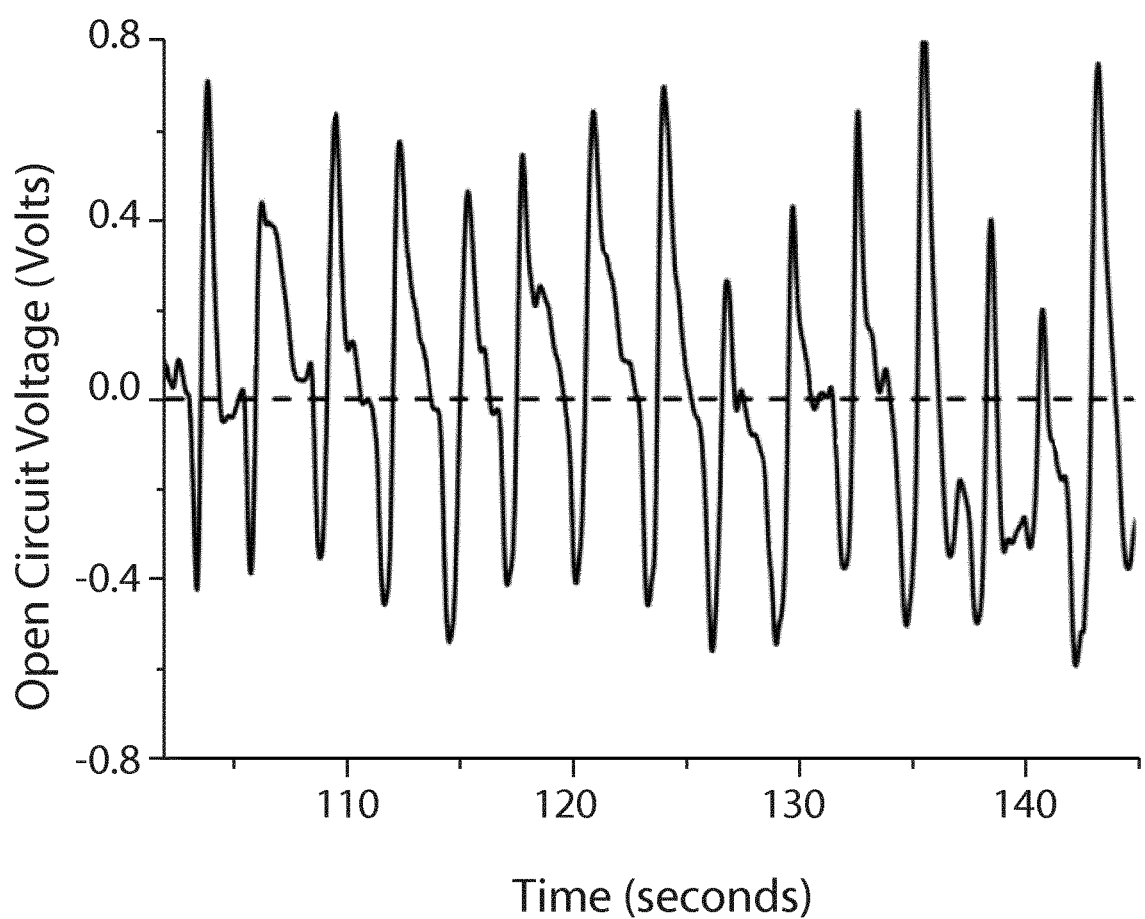
FIG. 13 shows the open circuit voltage harvested from DL-Alanine films under periodic manual compression.

In order to measure the open circuit voltage of the DL-Alanine films, wires were attached to the copper substrate with conductive silver paint, and connected to a multimeter. Periodic manual compression was applied, and the resulting voltages recorded. FIG. 13 shows the open circuit voltage harvested from DL-Alanine films under periodic manual compression. The voltage values varied from 190 mV to 800 mV, with an average output of 480 mV measured over a 40 second period. These voltages are twice as high as those measured for phage viruses and γ-glycine crystals, and four times as high as the layered 2D material molybdenum disulfide ($MoS_2$).

It will be appreciated that the piezoelectric properties of the amino acid crystals β and γ-glycine, as well as any of the 19 L-amino acid crystals, such as L-Threonine, L-Alanine, Hydroxy-L-Proline, L-Proline, and the racemic crystal DL Alanine, which have been demonstrated through the DFT calculations of the present invention could be exploited for use in a piezoelectric device. Accordingly, one aspect of the present invention comprises a piezoelectric device comprising an organic material in the form of one of these amino acid crystals. It should be understood that this piezoelectric device can produce sufficient piezoelectric energy for use in commercial applications, due to the fact that the device is optimised based on the results of the DFT calculations for the particular amino acid crystal. This optimisation includes the optimisation of the geometry of the crystal, which is achieved by slicing or cutting the crystal into the shape which has been determined from the DFT calculations to produce the maximum piezoelectric voltage from the amino acid crystal. The optimisation also includes aligning the crystallographic axes with the electrodes of the device in the manner determined from the DFT calculations which amplifies the piezoelectric voltage produced by the device. This piezoelectric device could be used in many technical applications, such as for example electromechanical transduction, sensing or energy harvesting.

Figure 5A:
FIG. 5A illustrates an energy harvesting method using γ-glycine crystals.
Figure 5B:
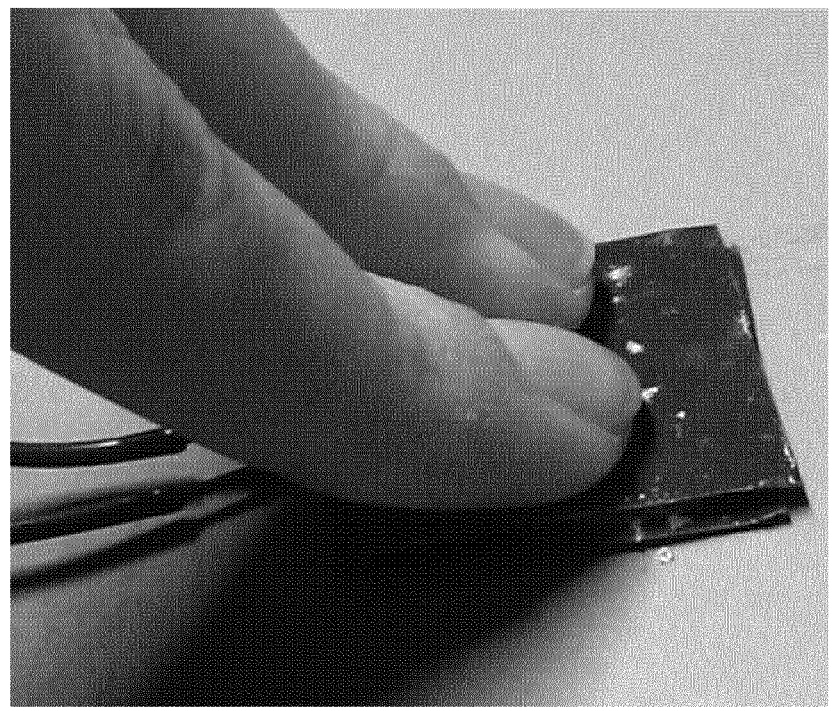
FIG. 5B shows a manual compression of the γ-glycine seed crystal layer shown in FIG. 5A.

One such simple energy harvesting device of the invention using γ-glycine crystals is shown in FIG. 5A. It can be seen from this figure that a layer of γ-glycine seed crystals has been deposited on an electrode and insulated. In one embodiment of this method, the electrode is a square copper electrode having dimensions of 18 mm×18 mm, and it is insulated with varnish. FIG. 5B shows a manual compression of the γ-glycine seed crystal layer of FIG. 5A. Full compression of the layer as shown averaged a force of 0.2 N.

Figure 6A:
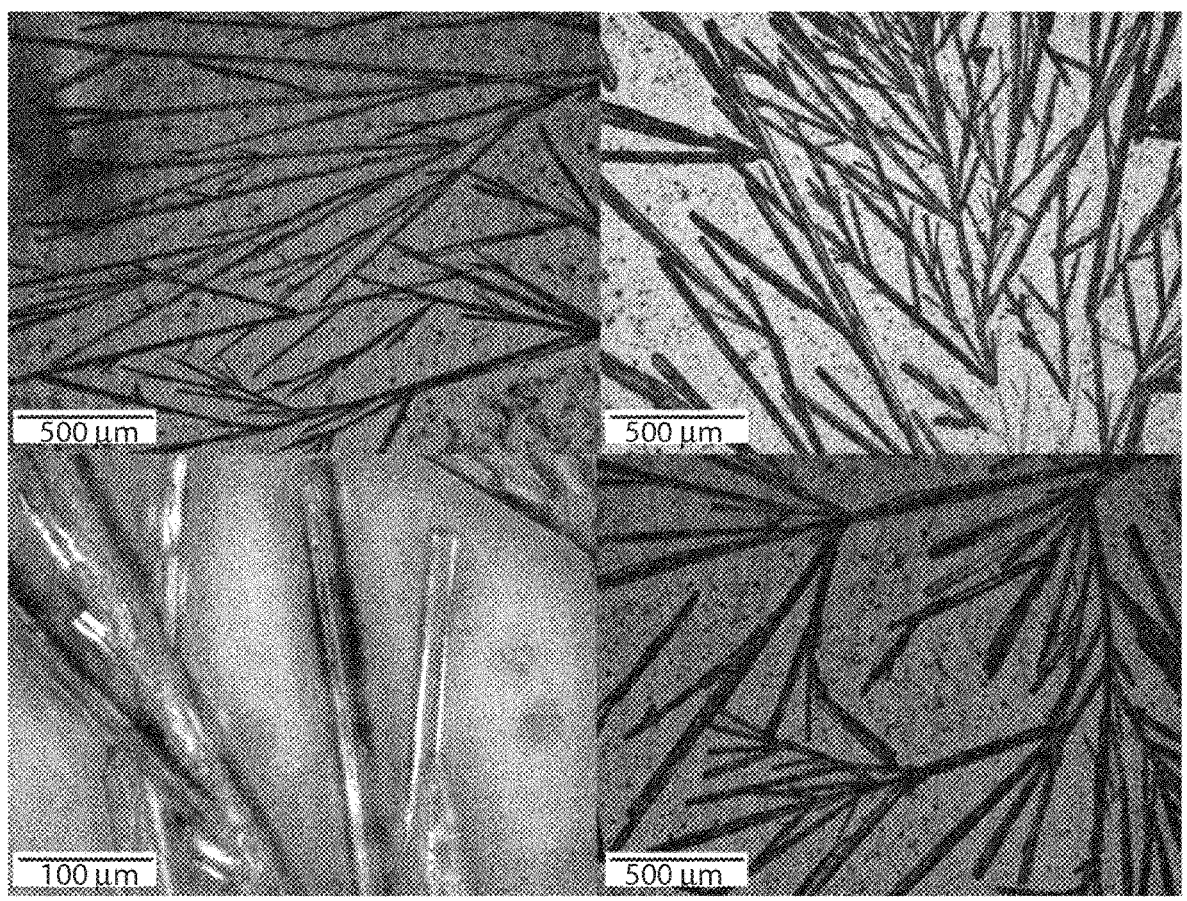
FIG. 6A illustrates the growth of β-glycine needles on a flexible substrate.
Figure 6B:
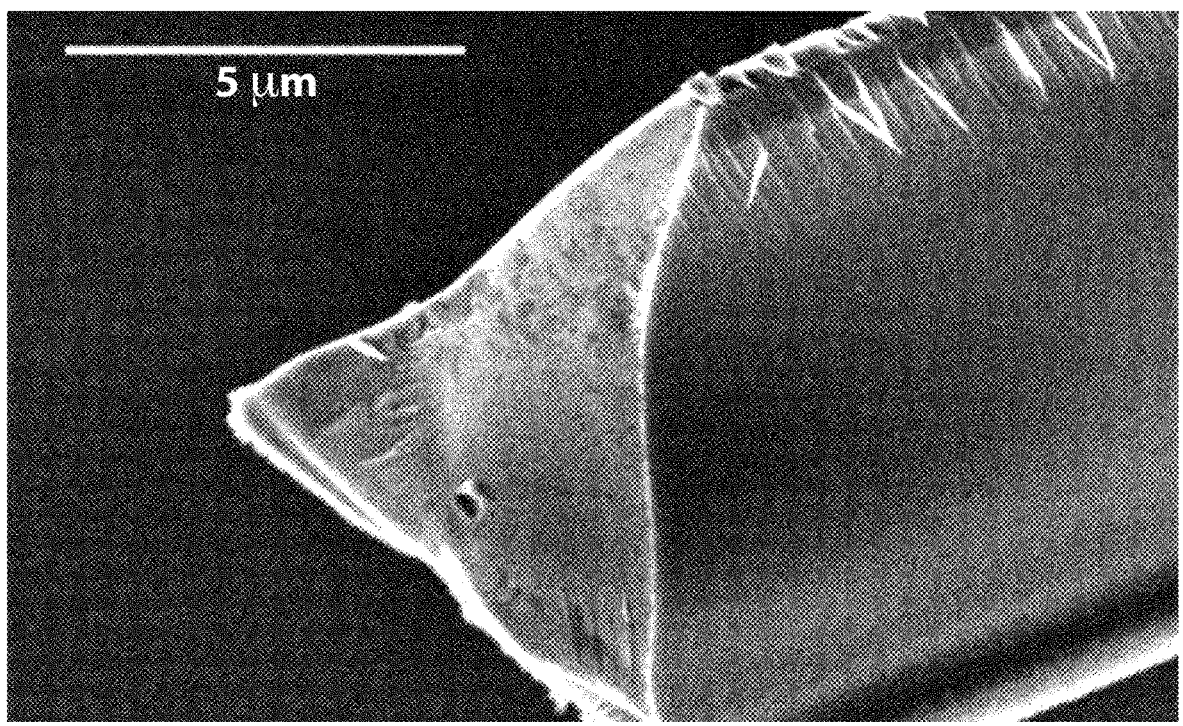
FIG. 6B shows morphologies of the glycine polymorphs as seen in a SEM for a cleaved β-glycine needle, lying at ninety degrees to the plane of growth.

FIG. 6A illustrates the growth of β-glycine needles on a flexible substrate, coated with ethanol to encourage the growth of this polymorph, and coated with PMMA resist, stabilising the needles and allowing for multiple layers of needles to be grown for a single piezoelectric device. FIG. 6B shows morphologies of the glycine polymorphs as seen in a Scanning Electron Micrograph (SEM) for a cleaved β-glycine needle, lying at ninety degrees to the plane of growth. These needles can then be sliced to make samples for transverse shear resonance measurements.

FIG. 7A shows a schematic of an exemplary embodiment of a simple resonator or energy harvester of the invention using a single crystal amino acid (i.e. a monocrystalline device), which in the figure shown is that of gamma glycine. It can be seen from this figure that the crystal is fixed between two metal electrodes along any of its crystallographic x, y or z axes. For use as an energy harvester, the electrodes may be connected for example to a LED. For use as a resonator, the electrodes can be connected so as to induce resonance in the crystal.

FIG. 7B shows a schematic of an exemplary embodiment of a stack actuator design using single amino acid crystals in accordance with the present invention. In the embodiment shown, single gamma glycine crystals of approximately 1 cm in diameter are used. FIG. 7C shows a schematic of another exemplary embodiment of a poly-crystalline stack actuator design, that is a design which uses amino acid films. In the embodiment shown, gamma glycine seed crystals are dispersed uniformly between electrodes.

FIG. 8A shows a schematic of an exemplary embodiment of an energy harvester in accordance with the present invention which exploits the $g_{16}$ piezoelectric constant of beta glycine shown in FIG. 2C. It can be seen from this figure that beta glycine and PMMA form a composite piezoelectric material. This material can be bent to induce a shear stress along the z-axis without destabilising the polymorph.

Figure 8B:
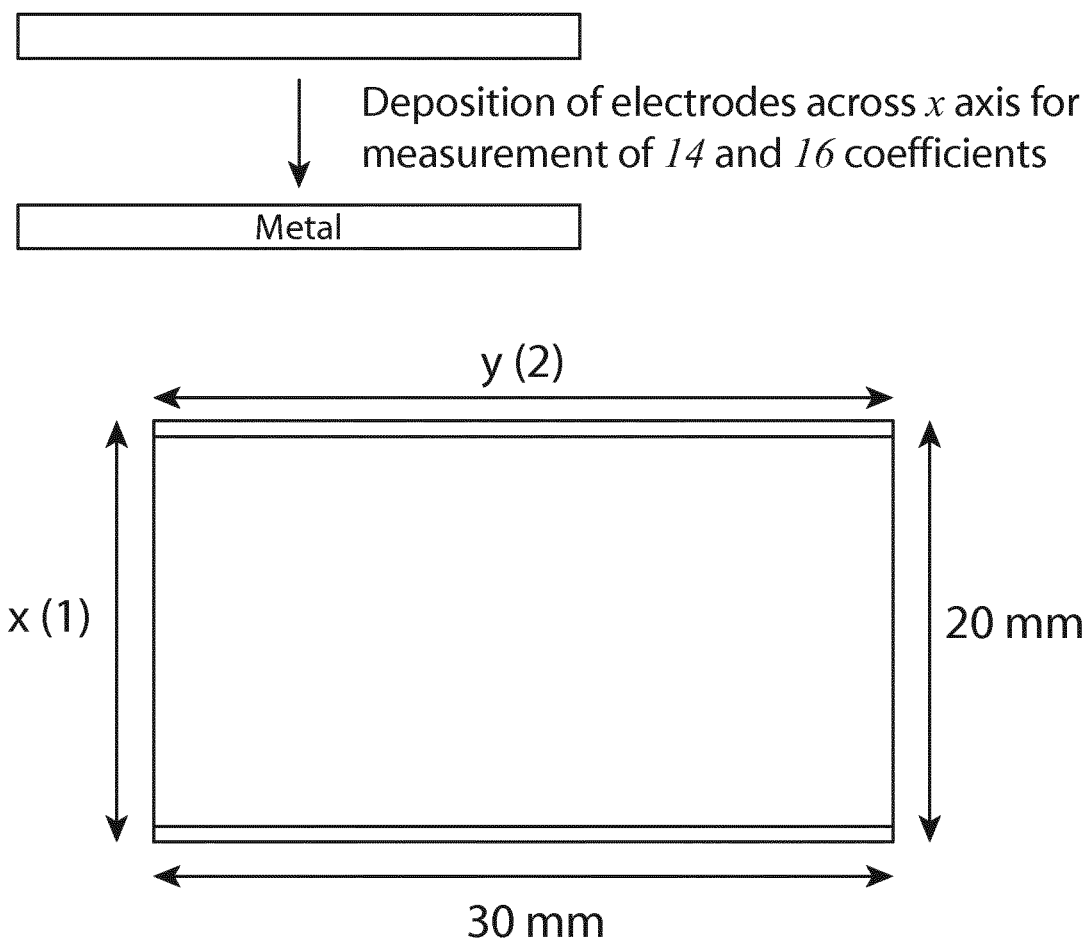
FIG. 8B shows a side view of the energy harvester of FIG. 8A showing the axis along which electrical contact is made as well as a top down view of the device.
Figure 8C:
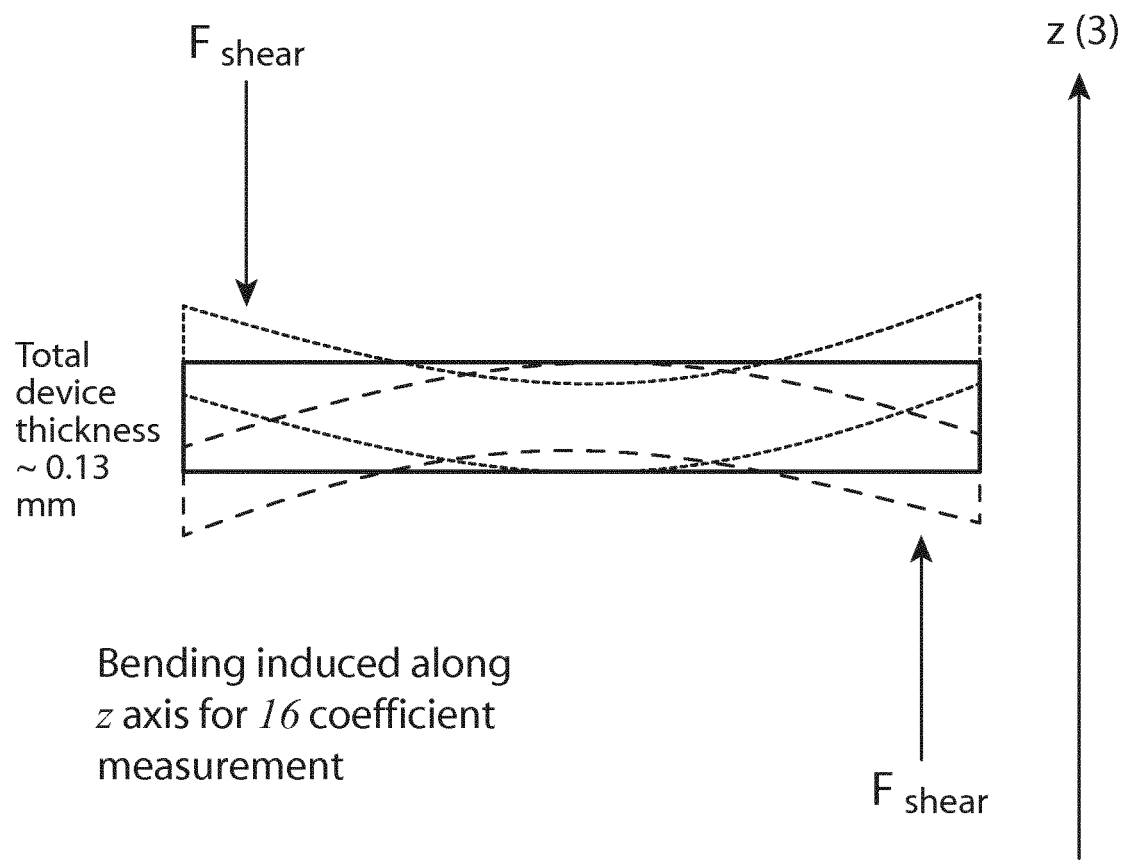
FIG. 8C shows a side view of the energy harvester of FIG. 8A showing the positive and negative forces that can be applied along the z axis to induce a shear stress.

FIG. 8B shows a side view of the energy harvester of FIG. 8A, showing the axis along which electrical contact is made, as well as a top down view of the device showing the x and y dimensions. FIG. 8C shows a side view of the energy harvester of FIG. 8A showing the positive and negative forces that can be applied along the z axis to induce a shear stress.

The amino acid crystal for the piezoelectric device of the present invention should be prepared in order to maximise the output of the device. This can include cutting or rotating the amino acid crystal at certain angles, such as the angles predicted by the DFT calculations. The required crystal geometry corresponds to the dimensions of the crystal which were determined from the DFT calculations to provide the optimum piezoelectric response from the crystal.

It can also include making electrical contact at precise locations on the crystal. In this regard, the orientation of the crystal should be such that its crystallographic axes are aligned with the electrodes of the device in a manner which has been determined from the DFT calculations to amplify the piezoelectric voltage produced by the crystal, and consequently the device.

Figure 9:
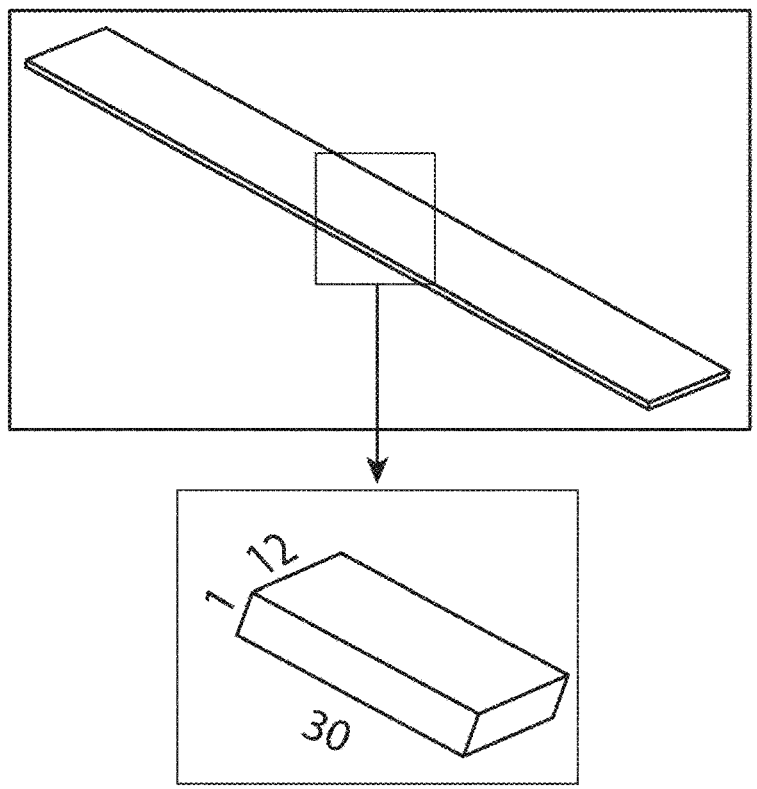
FIG. 9 shows a schematic (left) as well as the corresponding optical images (right) of monoclinic amino acid crystals illustrating the crystal cut required for piezoelectrically coupled electromechanical resonance to take place in the thickness shear mode.
Figure 9:
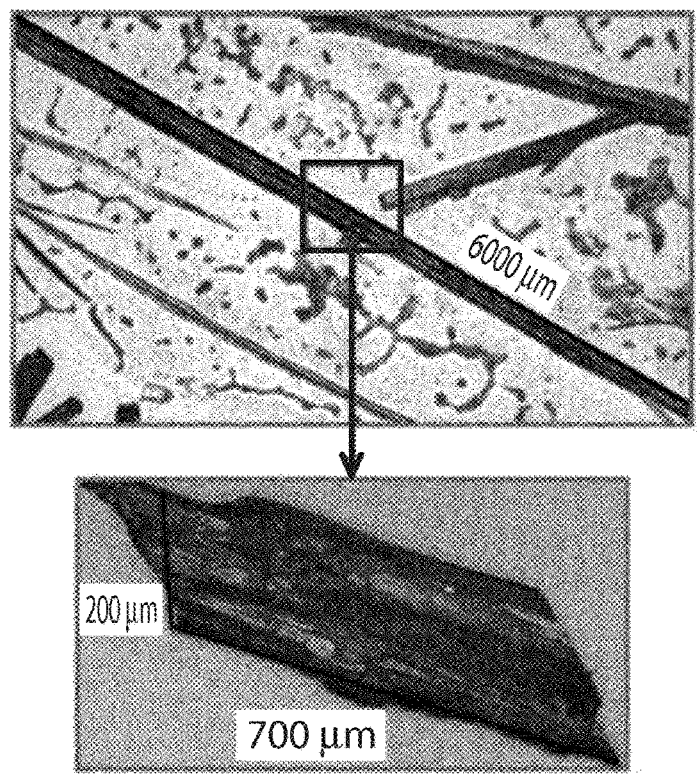

FIG. 9 shows a schematic (left) as well as the corresponding optical images (right) of monoclinic amino acid crystals, such as for example a monoclinic β glycine crystal, which details the crystal cut or geometry required for piezoelectrically coupled electromechanical resonance to take place in the thickness shear mode of the crystal, in order that the crystal can be used as a piezoelectric energy harvesting device for commercial applications. The crystal can be cut in any suitable manner in order to achieve this ratio, such as for example by hand. The ratio of the thickness, width and length in the samples is around 1:12:30 to within 5% due to sample roughness and variability. It should be appreciated that cuts of crystal which are not of this ratio give a negligible piezoelectric response. A typical slice measures ~200 μm width, ~700 μm length and <20 μm thickness.

The accuracy of the computational methods of the present invention were benchmarked with respect to three well-known inorganic piezoelectric materials, namely aluminium nitride (AlN), zinc oxide (ZnO) and α-quartz ($SiO_2$). In this regard, the elastic and piezoelectric coefficients of these materials determined by the DFT calculations of the present invention were compared with those obtained in previous experimental and computational studies. Once validated in this way, the same constants were calculated for the experimental X-ray structures of α, β and γ glycine. All crystal structures were optimised using conjugate gradient minimisation. A 4×4×4 gamma centred k-point grid was used for this, with a plane wave energy cut off of 600 eV.

One embodiment of performing the DFT calculations in respect of each of the piezoelectric coefficients in accordance with the present invention is described below. In each of these embodiments, the calculations were carried out using the Vienna Ab initio Simulation Package (VASP), using plane wave basis sets and the projector augmented-wave (PAW) method. Exchange-correlation effects were treated using density functional theory (DFT) via the Perdew, Burke, and Ernzerhof (PBE) implementation of the Generalised Gradient Approximation (GGA).

i. Calculation of Elastic Stiffness Tensor

In accordance with one embodiment of the invention, the elastic constants are calculated in the form of the stiffness tensor (C), presented as a 6×6 matrix:

$$C = \begin{pmatrix} \mathbf{c_{11}} & c_{12} & c_{13} & c_{14} & c_{15} & c_{16} \\ c_{21} & \mathbf{c_{22}} & c_{23} & c_{24} & c_{25} & c_{26} \\ c_{31} & c_{32} & \mathbf{c_{33}} & c_{34} & c_{35} & c_{36} \\ c_{41} & c_{42} & c_{43} & \mathbf{c_{44}} & c_{45} & c_{46} \\ c_{51} & c_{52} & c_{53} & c_{54} & \mathbf{c_{55}} & c_{56} \\ c_{61} & c_{62} & c_{63} & c_{64} & c_{65} & \mathbf{c_{66}} \end{pmatrix} \quad (1)$$

It is only necessary to extract the six primary diagonal matrix components, shown in bold in equation 1. The number of non-zero elements in both the elastic and piezoelectric matrices will vary according to the symmetry of the crystal being studied.

A finite differences method was used to calculate the stiffness tensor, with each atom being displaced in each direction by ±0.01 Å. An 8×8×8 gamma centred k-point grid was used. In this regard, it has been found that there is a negligible dependence of predicted elastic constant values on the number of k points used. The plane wave energy cut off is set to 1000 eV, to allow the stress tensor to fully converge due to the presence of oxygen and nitrogen atoms. Young's Moduli were derived from the stiffness matrix components. Values are presented as an average of three calculation methods.

ii. Calculation of Permittivity and Piezoelectric Tensors

In accordance with one embodiment of the invention, the piezoelectric strain constants and static dielectric tensors were calculated using Density Functional Perturbation Theory (DFPT). For this, an 8×8×8 gamma centred k point grid was also used, and the plane wave energy cut off was again 1000 eV. The accuracy of the resulting piezoelectric tensors was verified using a second, finite differences method and was also checked for van der Waals effects using dispersion corrections. Using the piezoelectric charge coefficients $e_{ij}$ which are calculated directly by VASP, and the elastic stiffness constants $c_{kj}$, it is possible to calculate the piezoelectric strain coefficient $d_{ik}$, using the relationship $$d_{ik}=e_{ij}/c_{kj} \quad (2)$$

Therefore the overall piezoelectric response can be described by a third rank tensor in the form of a 3×6 matrix:

$$\begin{pmatrix} d_{11} & d_{12} & d_{13} & d_{14} & d_{15} & d_{16} \\ d_{21} & d_{22} & d_{23} & d_{24} & d_{25} & d_{26} \\ d_{31} & d_{32} & d_{33} & d_{34} & d_{35} & d_{36} \end{pmatrix} \quad (3)$$

Here, $d_{11}$, $d_{22}$ and $d_{33}$ are defined as the longitudinal piezoelectric strain coefficients, with the final three columns containing the shear piezoelectric strain coefficients. The remaining matrix components represent the transverse piezoelectric strain coefficients, defined according to the direction of the applied stimulus, and the direction of the resulting response.

iii. Derivation of Voltage Constants

In accordance with one embodiment of the invention, the voltage constant $g_{ij}$ is obtained by dividing the corresponding piezoelectric strain constant $d_{ij}$ by the relevant dielectric constant $\varepsilon_{ii}$, as shown in equation 4. These constants are measured in V m/N.

$$g_{ij}=d_{ij}/\varepsilon_{ii}\varepsilon_o \quad (4)$$

Crystal Growth

In one embodiment of the invention, crystals of β-glycine were grown using a method similar to Seyedhosseini et al, by dissolving glycine powder in ultrapure water. Solutions were stirred and filtered, before being dropped onto clean glass slides using a micropipette. The droplets were left to dry in ambient conditions until crystallisation occurred. Beta needle aggregates ranging from 0.75 mm to 7 mm were grown in this manner. The crystals were grown and stored slightly below room temperature and humidity to inhibit transformation to the more stable α and γ polymorphs.

In one embodiment of the invention, crystals of γ-glycine were grown using the method of Bhat and Dharmaprakash. Glycine and sodium chloride were dissolved in ultrapure water in the ratio of 3:1. The solutions were filtered and heated in a water bath at constant temperature. When the volume was sufficiently reduced, seed crystals of approximately 1 mm in diameter were obtained by evaporation.

Physical Properties Formulae

Relevant physical properties were calculated using the formulae:

$$s_{66} = \frac{1}{4\rho v_A^2 l^2} \quad (5)$$

$$\varepsilon_{11} = \frac{c_{11}t}{A} \quad (6)$$

$$k_{16} = \frac{\pi}{2}\frac{v_R}{v_A}\cot\left(\frac{\pi}{2}\frac{v_R}{v_A}\right) \quad (7)$$

$$d_{16} = k_{16}\sqrt{\varepsilon_{11}s_{66}} \quad (8)$$

Here $s_{jk}$ is elastic compliance, ρ is density, $v_A$ is anti-resonance frequency, l is length, $\varepsilon_{ii}$ is static dielectric constant, C is capacitance, t is thickness, A is the electrode area, $k_{ij}$ is the electromechanical coupling constant, and $v_R$ is resonance frequency.

The electronic structure calculations of the present invention can accurately predict the piezoelectric behaviour of a broad range of inorganic and organic materials.

This computational prediction method of the present invention therefore can speed up the identification of candidate biomolecules for piezoelectricity, leading ultimately towards the re-engineering of these molecules as soft materials for applications in piezoelectric technologies.

This methodology for predicting piezoelectric coefficients demonstrates that both β and γ-glycine exhibit technologically significant piezoelectric responses. The confirmation of such a high piezoelectric coefficient in a material with relative low dielectric constant enables voltage constants to be predicted of up to two orders of magnitude larger than the best piezoelectric ceramics currently available.

Accordingly, the present invention also provides a piezoelectric device comprising an organic material. The organic material comprises an amino acid crystal such as β or γ-glycine. This piezoelectric device is suitable for use in many technical applications, such as for example electromechanical transduction, sensing or energy harvesting.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A piezoelectric device comprising:
a plurality of electrodes; and
an amino acid crystal coupled to the plurality of electrodes, wherein the amino acid crystal is sliced into a shape to maximise the piezoelectric voltage of the device, wherein the amino acid crystal comprises a monoclinic amino acid crystal sliced to a geometry such that the ratio of length to width to thickness of the crystal substantially corresponds to 30:12:1 so as to induce resonance of the crystal in thickness shear mode.

2. The piezoelectric device of claim 1, wherein the amino acid crystal comprises glycine.

3. The piezoelectric device of claim 2, wherein the amino acid crystal comprises/β-glycine.

4. The piezoelectric device of claim 2, wherein the amino acid crystal comprises γ-glycine.

5. The piezoelectric device of claim 1, wherein the amino acid crystal comprises a crystal selected from the group of nineteen L-amino acid crystals or the racemic crystal DL-Alanine.

6. The piezoelectric device of claim 1, wherein the crystallographic axes of the amino acid crystal are aligned with the plurality of electrodes.

7. The piezoelectric device of claim 1, wherein the geometry of the amino acid crystal and the orientation of the amino acid crystal are determined from piezoelectric coefficients predicted by a quantum mechanical calculation performed on the amino acid crystal.

8. The piezoelectric device of claim 7, wherein the quantum mechanical calculation is based on Density Functional Theory (DFT).

9. An electromechanical transducer comprising the piezoelectric device of claim 1.

10. A sensor comprising the piezoelectric device of claim 1.

11. An energy harvester comprising the piezoelectric device of any of claim 1.

12. The piezoelectric device of claim 1, further comprising a flexible substrate coated with ethanol, wherein the amino acid crystal is grown in a plurality of layers on the substrate.

* * * * *